United States Patent
Coates et al.

(10) Patent No.: US 9,085,632 B2
(45) Date of Patent: Jul. 21, 2015

(54) BIOLOGICAL MATERIALS AND USES THEREOF

(75) Inventors: Anthony Robert Milnes Coates, London (GB); Yanira Riffo-Vasquez, London (GB); Peter Tormay, London (GB)

(73) Assignee: PEPTINNOVATE LIMITED, London (GB)

( * ) Notice: Subject to any disclaimer, the term of this patent is extended or adjusted under 35 U.S.C. 154(b) by 441 days.

(21) Appl. No.: 12/918,789

(22) PCT Filed: Feb. 25, 2009

(86) PCT No.: PCT/GB2009/000522
§ 371 (c)(1),
(2), (4) Date: Nov. 17, 2010

(87) PCT Pub. No.: WO2009/106819
PCT Pub. Date: Sep. 3, 2009

(65) Prior Publication Data
US 2011/0052616 A1    Mar. 3, 2011

(30) Foreign Application Priority Data
Feb. 25, 2008 (GB) .................................. 0803369.8

(51) Int. Cl.
*C07K 5/10* (2006.01)
*A61K 38/00* (2006.01)
*C07K 14/35* (2006.01)

(52) U.S. Cl.
CPC *C07K 14/35* (2013.01); *A61K 38/00* (2013.01)

(58) Field of Classification Search
None
See application file for complete search history.

(56) References Cited

FOREIGN PATENT DOCUMENTS

| EP | 1 693 068 A1 | 8/2006 |
|---|---|---|
| GB | 2 391 477 A | 2/2004 |
| WO | WO 02/40037 A2 | 5/2002 |
| WO | WO 02/40517 A3 | 5/2002 |

OTHER PUBLICATIONS

Gura, Science, 1997, 278:1041-1042.*
Kaiser, Science, 2006, 313, 1370.*
Bellone et al, Immunology Today, 1999, 20:457-462.*
Granziero et al, Eur. J. Immunol. 1999, 29:1127-1138.*
Byers, T, CA Journal, vol. 49, No. 6, Nov./Dec. 1999.*
Lewthwaite, J. C. et al., *Mycobacterium tuberculosis* Chaperonin 60.1 Is a More Potent Cytokine Stimulator than . . . Doman, Infection and Immunity, 69(12):7349-7355 (Dec. 2001).

* cited by examiner

*Primary Examiner* — Mark Halvorson
(74) *Attorney, Agent, or Firm* — Steptoe & Johnson LLP

(57) ABSTRACT

The present invention concerns a peptide molecule or a nucleic acid molecule, for use in medicine and, in particular, for use in preventing or treating a non-cancerous condition or relieving pain in a patient. The invention also relates to a pharmaceutical composition comprising the peptide or nucleic acid molecule of the invention and methods of treatment thereof.

4 Claims, 27 Drawing Sheets

Figure 25 continued

Figure 1:
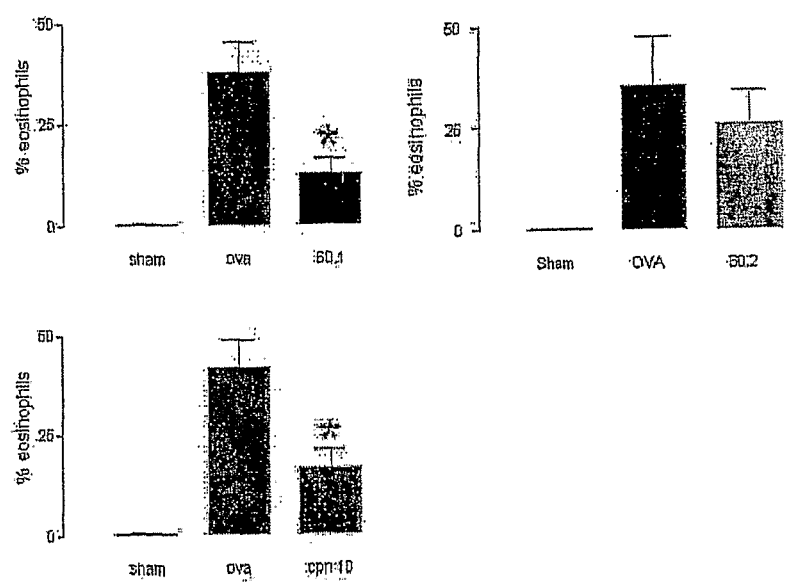

| | Peptide | Position (in respect of full-length protein) | Comment |
|---|---|---|---|
| 1 | MSKLIEYDETARRAMEVGMDKLADTVRVT | 1-29 (SEQ ID NO: 1) | First 30 amino acids of the protein. Contains half a β-sheet and a alpha-helix. Highly surface exposed |
| 2 | LGPRGRHVVLAKAFGGPTVTN | 30-50 (SEQ ID NO: 2) | Comprises a β-sheet in the structure. Highly surface exposed |
| 3 | DGVTVAREIELEDPFEDLGAQLVKSVATKTNDV | 51-83 (SEQ ID NO: 3) | Comprises of 2 alpha-helices within the structure. Exposed to the "inner side" of a putative oligomeric structure (unknown whether oligomeric structure exists) |
| 4 | AGDGTTTATILAQALIKGGLRLVAAGVN | 84-110 (SEQ ID NO: 4) | Comprises of a single alpha-helix. Only partly exposed. Runs through the centre of the domain |
| 5 | PIALGVGIGKAADAVSEALLASAIP | 111-136 (SEQ ID NO:5) | Comprises of a single alpha-helix. Highly surface exposed |
| 6 | EEGIVPGGGASLIHQARKALTELRASL | 406-432 (SEQ ID NO: 6) | Comprises of one half of a β-sheet, an alpha helix and an linker region. Partly (β-sheet) buried in the structure |
| 7 | TGDEVLGVDVFSEALAAPLFWIAANAGL | 433-460 (SEQ ID NO: 7) | Comprises of two alpha-helices. Highly surface exposed. This area is one of the regions with high dissimilarity with Cpn60.2 |
| 8 | DGSVVNKVSELPAGHGLNVNTLSYGDLAAD | 461-491 (SEQ ID NO: 8) | Comprises of an alpha helix, a β-sheet and another alpha helix. Highly surface exposed |
| 9 | GVIDPVKVTRSAVLNASSVARMVLTTETVVV | 492-522 (SEQ ID NO: 9) | Highly surface exposed towards the inner face of a putative oligomeric structure. Contains one half of a β sheet. |
| 10 | LTTETVVVDKPAKAEDHDHHHGHAH | 515-539 (SEQ ID NO: 10) | Last 25 aa. Not visible in the putative structure. Seems to be flexible and could therefore not be resolved in the *E. coli* structure. This is another area of high dissimilarity with Cpn60.2 |

Figure 25 continued

Examples of peptides and purity of manufacture

| Sequence | Name | Code | Purity | List number |
|---|---|---|---|---|
| LGPRGRHVVLAKAFGGPTVTN (SEQ ID NO: 2) | p60.1_30 | M1429-A1 | 96 % | 2 |
| EEGIVPGGGASLIHQARKALTELRASL (SEQ ID NO: 6) | p60.1_406 | M1429-A2 | 99 % | 6 |
| TGDEVLGVDVFSEALAAPLFWIAANAGL (SEQ ID NO: 7) | 30.1_433 | M1429-A3 | 96 % | 7 |
| DGSVVVNKVSELPAGHGLNVVNTLSYGDLAAD (SEQ ID NO: 8) | p60.1_461 | M1429-A4 | 96 % | 8 |
| GVIDPVKVTRSAVLNASSVARMVLTTETVW (SEQ ID NO: 9) | p60.1_492 | M1429_A5 | | 9 |
| LTTETVWDKPAKAEDHDHHHGHAH (SEQ ID NO: 10) | p60.1_515 | M1429-A6 | 98.5 % | 10 |

BIOLOGICAL MATERIALS AND USES THEREOF

CLAIM OF PRIORITY

This application claims priority under 35 USC 371 to International Application No. PCT/GB2009/000522, filed on Feb. 25, 2009, which claims priority to Great Britain Application Serial No. 0803369.8, filed Feb. 25, 2008, each of which is incorporated by reference in its entirety.

The present invention relates to polypeptides deriving from chaperonin 60.1 and their uses in the treatment of disease and as pain relief agents.

Heat shock polypeptides are a family of molecules found in all organisms, whose function is to aid the biological processing and stability of biological molecules (Zugel & Kauffman (1999) *Role of heat shock polypeptides in protection from and pathogenesis of infectious diseases*. Clin. Microbiol. Rev. (12)1: 19-39; Ranford et al. (2000) *Chaperonins are cell signalling polypeptides: —the unfolding biology of molecular chaperones*. Exp. Rev. Mol. Med., 15 September, www-.ermn.cbcu.cam.ac.uk/00002015h.htm).

Heat shock polypeptides are located in every cellular compartment, and possess the ability to interact with a wide range of biological molecules. In particular, the heat shock polypeptides aid and influence polypeptide folding and polypeptide translocation at any time from assembly through to disassembly of the polypeptide and any complexes thereof. The helper nature of the heat shock polypeptides has led to them to also being known as molecular chaperones (Laskey et al. (1978) *Nucleosomes are assembled by an acidic polypeptide, which binds histones and transfers them to DNA*. Nature (275): 416-420).

Heat shock polypeptides are synthesised by cells in response to environmental stress, which includes, but is not limited to temperature changes (both increases and decreases), and pathophysiological signals such as cytokines. In response to the environmental stress, heat shock polypeptides use their ability to process other polypeptides to protect such polypeptides from any denaturation that may occur due to the presence of the stress. This mechanism also serves to protect cells which contain the protein.

Chaperonin polypeptides are a subgroup of heat shock polypeptides whose role in polypeptide folding is well known. There are two families of chaperonin polypeptide, the chaperonin 60 (approximately 60 kDa) and chaperonin 10 (approximately 10 kDa) families (Ranford, 2000). The best characterised chaperonins are those derived from *E. coli*, from which the characteristic structure of chaperonin 60 and chaperonin 10 has been established. The chaperonin complexes of most other organisms also substantially conform to this characteristic structure.

The characteristic structure of chaperonins is a complex formed from two heptamer rings (composed of seven chaperonin 60 monomers) which face one another and are capped by a heptamer ring composed of chaperonin 10 monomers.

Conventionally, chaperonins assist polypeptide folding when the target polypeptide enters the central core of the ringed heptamers, and on the subsequent release of energy from ATP the target polypeptide is released from the central core by a conformational change in the chaperonin structure (Ranson et al. (1998) *Review Article: Chaperones*. Biochem. J. (333): 233-242).

*Mycobacterium tuberculosis* (*M. tuberculosis*) produces Chaperonin 60.1 (cpn 60.1), a polypeptide that is named based on its amino acid sequence identity to other known chaperonins. Further *M. tuberculosis* chaperonin polypeptides are chaperonin 10 (cpn 10) and chaperonin 60.2 (cpn 60.2). Chaperonin 60.2 exhibits 59.6% amino acid sequence identity and 65.6% nucleic acid sequence identity to cpn 60.1.

The present invention relates to the use of fragments of chaperonin 60.1 or functionally equivalent molecules from *Mycobacterium tuberculosis* or related prokaryotes in the prevention and/or treatment of both cancerous and non-cancerous conditions. Examples of non-cancerous conditions include autoimmune disorders, osteoporosis, allergic disorders or conditions of immunoactivation, particularly asthma, and/or conditions typified by a T helper lymphocyte 2 (Th2)-type immune response and/or conditions associated with eosinophilia and methods of stimulating the production of immune response mediators, e.g. cytokines, in vitro or in vivo.

Autoimmunity reflects the loss of tolerance to "self" resulting in inappropriate destruction of normal cells or tissue. In many conditions, autoantibodies are found, but may reflect an effect rather than cause of a disease. In some diseases however autoantibodies are the first, major, or only detectable abnormality. One class of molecules which is implicated in this respect are the chaperonins which are highly immunogenic. Chaperonins belong to a group of proteins called molecular chaperones which bind non-native proteins and assist them, in an ATP-dependent catalytic process, to fold into the correct three-dimensional form required for a functional protein.

Chaperonins are believed to stimulate the immune system at many levels simultaneously, including monocytes, macrophages, fibroblast-like cells, perhaps other types of cells, and T cells. The immune defences in mammals may be divided into the "innate" and "adaptive" defences. Those which are already in place, such as phagocytes, natural killer cells and complement are considered innate. On challenge, adaptive immunity is activated in the form of B and T lymphocytes. Chaperonins are known to act directly on the innate defence mechanisms, particularly on phagocytes. They also stimulate a powerful adaptive immune response, namely the production of antibody and the stimulation of T lymphocytes which in some cases may be protective. Notably they induce cytokine secretion which is thought to be important for host defences. In some cases however it is believed that the presence of chaperonins may be damaging to the host.

Chaperonins' role in autoimmune disease is controversial. Although infection/immunity with chaperonin-containing organisms is universal, and healthy people have T cell responses to self-chaperonins, including the production of chaperonin-specific antibodies, classical autoimmune disease is quite uncommon. So the presence of immune reactions to chaperonins may be incidental and unimportant.

The theory of molecular mimicry however suggests the involvement of chaperonins in autoimmune disease and is based on the high level of amino acid sequence conservation between chaperonins of microbial and mammalian origin. The theory proposes that during infection with a wide range of microbes, chaperonin epitopes that are shared between microbes and mammals stimulate T lymphocytes. According to this theory a high level of chaperonin presentation of shared chaperonin epitopes breaks tolerance to self-chaperonins and autoimmune disease develops.

Chaperonins obtained from tumours have been found to result in necrotic effects on those tumours. It is suggested that this may be achieved through enhancing immunological recognition of tumour antigens although the mechanism of this is not known. It therefore appears that chaperonins induce protective adaptive immunity against bacterial infection and cancer.

Allergic reactions, such as asthma, concern proportionally inappropriate or misdirected immune responses. The prevalence of asthma for example is increasing and effective therapies for treating all cases have not yet been found. Current treatment often uses immunosuppressive glucocorticosteroids, beta agonists, cromoglycate, leukotriene modifiers etc. which have numerous side-effects.

In such allergic reactions, high IgE levels occur and T helper lymphocyte-2 (Th2) immune responses predominate over Th1 responses resulting in an inflammatory response. Th1 responses are thought to be mainly protective against microbial infection and are promoted by cytokines, particularly interleukin-12 (IL-12), IL-2 and interferon-γ. In contrast, Th2 responses, in the appropriate genetic background, are associated with harmful allergic tissue damage.

However, it has been suggested that in other conditions such as autoimmune disorders, e.g. adjuvant arthritis, over-active ThI responses are causal of the disorder. Conversion of ThI to Th2 or Th2 to ThI responses may therefore have utility in treating the above described disorders.

Whilst it has been known that bacteria such as *L. monocytogenes, M. bovis,* and *M. tuberculosis* can convert Th2 to ThI responses, the molecules which is(are) responsible for this conversion have not been identified.

Suggestions in the art have however implicated a heat shock protein, hsp65, from *M. leprae* which is able to induce Th1 responses (Lowrie et al., 1999, Nature, 400, p269-271; Bonato et al., 1998, Infect. Immun., 66, p169-175). The homologue, hsp65 from *M. tuberculosis,* has the ability to stimulate human monocytes to synthesize pro-inflammatory cytokines and activate monocytes and human vascular endothelial cells (Friedland et al., 1993, Clin. Exp. Immunol., 91, p5862; Peetermans et al., 1995, Infect. Immun., 63, p3454-3458; Verdegaal, et al., 1996, J. Immunol., 157, p369-376).

The present invention also relates to the use of fragments of chaperonin 60.1 or functionally equivalent molecules from *Mycobacterium tuberculosis* or related prokaryotes in the relief of pain.

Pain relief is usually achieved by oral or parenteral medication. Effective pain relief can be achieved in most cases with widely known pain relief drugs such as paracetamol, aspirin and other non-steroidal anti-inflammatory drugs (NSAIDS) such as ibuprofen, and cylooxygenase-2-selective inhibitors (CSIs). Narcotic analgesics act on specific receptors in the Central Nervous System (CNS). Codeine and dihydrocodeine are moderately potent narcotic analgesics and have a low potential for addiction. Other more potent narcotic analgesics, such as morphine and methadone can be used to control severe pain.

A variety of problems exist with presently known pain relief agents. The drugs are relatively short acting and analgesia lasts for only a few hours. Repeated doses of the drug are usually necessary to control the pain. Sub-optimal pain relief is another common problem, leading to the patient increasing the dose, or changing medication. In the case of NSAIDS, unpleasant gastrointestinal side-effects such as dyspepsia and ulcers are common, and about two-thirds of users change brands of NSAIDS at least once because of adverse effects and poor efficacy (Steinfeld S and Bjorke P A. Results from a patient survey to assess gastrointestinal burden of non-steroidal anti-inflammatory drug therapy contrasted with a review of data from EVA to determine satisfaction with rofecoxib. Rheumatology (Oxford) 2002, 41(S1), 23-27.). In addition, NSAIDs and CSIs can give rise to cardiovascular complications (Hillis W S, (2000) Areas of emerging interest in analgesia: cardiovascular complications. Am. J. Ther. 9 (3) 259-69). Aspirin can cause Reye Syndrome in a small proportion of children, and thus aspirin is not available for use in children. Paracetamol has to be used with caution since, an overdose, is hepatotoxic (Cranswick, N., Coghlan D. Paracetamol efficacy and safety in children: the first 40 years (2000) Am. J. Ther. 7(2) 135-41). Narcotic analgesics have a variety of side-effects including drowsiness, constipation, nausea, headache and vertigo. Repeated administration of potent narcotic analgesics such as morphine can cause addiction.

An advantage of chaperonins as pain relief agents over current pain relief drugs is that they may have fewer adverse side-effects. It has been estimated that two billion people carry *M. tuberculosis* without developing Tuberculosis. Carriage of *M. tuberculosis* has not been associated with the side effects which are seen with commonly known pain-relief medication such as gastro-intestinal side-effects, cardiovascular complications, hepatotoxicity, Reye Syndrome or addiction.

A further advantage over previously known pain relief agents is that, the analgesic affect of chaperonins will last longer.

Against this background, the present inventors have now surprisingly identified peptides and polypeptide fragments of the chaperonin protein Chaperonin 60.1 (also referred to herein as Cpn60.1) of *Mycobacterium tuberculosis* that are capable of treating both cancerous and no-cancerous conditions and also of providing pain relief in vivo and in vitro.

Thus, in a first aspect, the invention provides an isolated or recombinant peptide molecule comprising or consisting of a polypeptide sequence selected from the group:

| | |
|---|---|
| (i) | MSKLIEYDETARRAMEVGMDKLADTVRVT; (SEQ ID NO: 1) |
| (ii) | LGPRGRHVVLAKAFGGPTVTN; (SEQ ID NO: 2) |
| (iii) | DGVTVAREIELEDPFEDLGAQLVKSVATKTNDV; (SEQ ID NO: 3) |
| (iv) | AGDGTTTATILAQALIKGGLRLVAAGVN; (SEQ ID NO: 4) |
| (v) | PIALGVGIGKAADAVSEALLASATP; (SEQ ID NO: 5) |
| (vi) | EEGIVPGGGASLIHQARKALTELRASL; (SEQ ID NO: 6) |
| (vii) | TGDEVLGVDVFSEALAAPLFWIAANAGL; (SEQ ID NO: 7) |
| (viii) | DGSVVVNKVSELPAGHGLNVNTLSYGDLAAD; (SEQ ID NO: 8) |
| (ix) | GVIDPVKVTRSAVLNASSVARMVLTTETVVV; (SEQ ID NO: 9) |
| (x) | LTTETVVVDKPAKAEDHDHHHGHAH. (SEQ ID NO: 10) |

(xi) a polypeptide sequence which has more than 66% or 70% or 75% or 80% or 85% or 90% or 95% identity to a polypeptide sequence defined in any of (i) to (x) and has a function equivalent to a polypeptide sequence defined in any of (i) to (x); and (xii) a fragment of a polypeptide sequence defined in any of (i) to (xi) which has a function equivalent to a polypeptide sequence defined in any of (i) to (xi).

By "polypeptide" we also include peptides, proteins and peptidomimetic compounds. The term "peptidomimetic" refers to a compound that mimics the conformation and desirable features of a particular peptide as a therapeutic agent, but that avoids the undesirable features.

By "a function equivalent to a polypeptide sequence defined in any of (i) to (x)" we include any peptide, polypeptide and/or fragment thereof which possesses a functional activity identical or substantially similar to any function displayed by or attributed to the defined polypeptide sequence. For example, the polypeptide sequences defined in (i) to (x) may exhibit anti-inflammatory properties (as exemplified in the accompanying examples) permitting their use in the prevention and/or treatment of a non-cancerous condition, or in the relief of pain.

Functional equivalence can be measured using, for example, methods described in the accompanying examples (for example by measuring paw latency on a heated plate; or measuring the release of inflammatory cytokines in vivo or in vitro).

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e.g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Fragments of the proteins of the present invention which are capable of exhibiting biological activity are also encompassed by the present invention. Fragments of the protein may be in linear form or they may be cyciized using known methods, for example, as described in H. U. Saragovi, et al., Bio/Technology 10, 773-778 (1992) and in R. S. McDowell, et al., *J. Amer. Chem. Soc.* 114, 9245-9253 (1992), both of which are incorporated herein by reference. Such fragments may be fused to carrier molecules such as immunoglobulins for many purposes, including increasing the valency of protein binding sites.

The invention further provides an isolated or recombinant nucleic acid molecule comprising or consisting of a polynucleotide sequence selected from the group:

(a) a polynucleotide sequence which encodes a polypeptide sequence selected from the group consisting of:

| (i)   | MSKLIEYDETARRAMEVGMDKLADTVRVT; (SEQ ID NO: 1) |
| (ii)  | LGPRGRHVVLAKAFGGPTVTN; (SEQ ID NO: 2) |
| (iii) | DGVTVAREIELEDPFEDLGAQLVKSVATKTNDV; (SEQ ID NO: 3) |
| (iv)  | AGDGTTTATILAQALIKGGLRLVAAGVN; (SEQ ID NO: 4) |
| (v)   | PIALGVGIGKAADAVSEALLASATP; (SEQ ID NO: 5) |

| | |
|---|---|
| (vi) | EEGIVPGGGASLIHQARKALTELRASL;<br>(SEQ ID NO: 6) |
| (vii) | TGDEVLGVDVFSEALAAPLFWIAANAGL;<br>(SEQ ID NO: 7) |
| (viii) | DGSVVVNKVSELPAGHGLNVNTLSYGDLAAD;<br>(SEQ ID NO: 8) |
| (ix) | GVIDPVKVTRSAVLNASSVARMVLTTETVVV;<br>(SEQ ID NO: 9) |
| (x) | LTTETVVVDKPAKAEDHDHHHGHAH.<br>(SEQ ID NO: 10) |

(b) a polynucleotide sequence which has more than 66% or 70% or 75% or 80% or 85% or 90% or 95% identity to a polynucleotide sequence defined in (a); or a polynucleotide sequence which hybridizes to a polynucleotide sequence defined in (a) under conditions of 2×SSC, 65° C. which encodes a polypeptide sequence having a function equivalent to a polypeptide sequence defined in any of (i) to (x); and (c) a fragment of a polynucleotide sequence defined in (a) or (b) which encodes a polypeptide sequence having a function equivalent to a polypeptide sequence defined in any of (i) to (x).

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of the invention can be obtained by screening appropriate cDNA or genomic DNA libraries under suitable hybridization conditions using any of the polynucleotides of the invention or a portion thereof as a probe. Alternatively, the polynucleotides of the invention may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, more typically at least about 85%, 86%, 87%, 88%, 89%, more typically at least about 90%, 91%, 92%, 93%, 94%, and even more typically at least about 95%, 96%, 97%, 98%, 99% sequence identity to a polynucleotide recited above.

Included within the scope of the nucleic acid sequences of the invention are nucleic acid sequence fragments that hybridize under stringent conditions to any of the nucleotide sequences of the invention, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to) any one of the polynucleotides of the invention are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in the invention, a representative fragment thereof, or a nucleotide sequence at least 90% identical, preferably 95% identical, to the invention with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1.times. SSC/0.1% SDS at 68° C.), and moderately stringent conditions (i.e., washing in 0.2.times. SSC/0.1% SDS at 42° C.). Other exemplary hybridization conditions are described herein in the examples.

In instances of hybridization of deoxyoligonucleotides, additional exemplary stringent hybridization conditions include washing in 6.times. SSC/0.05% sodium pyrophosphate at 37° C. (for 14-base oligonucleotides), 48° C. (for 17-base oligos), 55° C. (for 20-base oligonucleotides), and 60° C. (for 23-base oligonucleotides).

SSC is defined as 0.15M NaCl, 0.015M Sodium Citrate, pH 7.2

By "identity" we mean the number or percentage (dependent on presentation of the results) of amino acid residues or nucleic acid residues in a candidate sequence that are identical with the amino acid residues or nucleic acid residues of the sequence of interest, after aligning the sequences and introducing gaps, if necessary to achieve maximum percent sequence identity, and not considering any conservative substitutions as part of the sequence identity.

The percentage sequence identity between two polynucleotides or polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) Nucleic Acids Res. 22, 4673-80). The parameters used may be as follows: fast pairwise alignment parameters: K-tuple(word) size; 1, window size; 5, gap penalty; 3, number of top diagonals; 5. Scoring method: x percent; multiple alignment parameters: gap open penalty; 10, gap extension penalty; 0.05. Scoring matrix: BLOSUM.

As used herein, "substantially equivalent" or "substantially similar" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 85% sequence identity, more preferably at least 90% sequence identity, more preferably at least 95% sequence identity, more preferably at least 98% sequence identity, and most preferably at least 99% sequence identity. Substantially equivalent nucleotide sequence of the invention can have lower percent sequence identities, taking into account, for example, the redundancy or degeneracy of the genetic code. Preferably, the nucleotide sequence has at least about 65% identity, more preferably at least about 75% identity, more preferably at least about 80% sequence identity, more preferably at least 85% sequence identity, more preferably at least 90% sequence identity, more preferably at least about 95% sequence identity, more preferably at least 98% sequence identity, and most preferably at least 99% sequence identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) *Methods Enzymol.* 183:626-645). Identity between sequences can also be determined by other methods known in the art, e.g. by varying hybridization conditions.

The invention further provides a peptide molecule according to the invention for use in medicine and/or a nucleic acid molecule according to the invention for use in medicine.

Preferably, the invention provides a peptide molecule according to the invention and/or a nucleic acid molecule according to the invention for use in preventing and/or treating a non-cancerous condition or a cancerous condition.

The invention further provides the use of a peptide molecule or a nucleic acid molecule of the invention in the manufacture of a medicament for preventing and/or treating a non-cancerous condition or a cancerous condition.

In a further aspect, the invention provides a pharmaceutical composition comprising or consisting of a peptide molecule according to the invention and a pharmaceutically-acceptable excipient.

In a further aspect, the invention provides a pharmaceutical composition comprising or consisting of a nucleic acid molecule according to the invention and a pharmaceutically-acceptable excipient.

The molecules, medicaments and pharmaceutical compositions of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The molecules, medicaments and pharmaceutical compositions of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions' of the invention. A device which delivers a pulsed electric field to cells increases the permeability of the cell membranes to the drug, resulting in a significant enhancement of intracellular drug delivery.

The molecules, medicaments and pharmaceutical compositions of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the molecules, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The molecules, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the nucleic acids, molecules and pharmaceutical formulations of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The molecules, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

Preferably, the medicament and/or pharmaceutical composition of the present invention is a unit dosage containing a daily dose or unit, daily sub-dose or an appropriate fraction thereof, of the active ingredient.

The molecules, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the molecules, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the molecules, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The molecules, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

The molecules, medicaments and pharmaceutical compositions of the invention can also be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the molecules, medicaments and pharmaceutical compositions of the invention will usually be from 0.1 to 100 mg per adult per day administered in single or divided doses.

Thus, for example, the tablets or capsules of the molecules of the invention may contain from 0.1 mg to 100 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The molecules, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A, or 1,1,1,2,3,3,3-heptafluoropropane (HFA 227EA), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains at least 0.1 mg of a molecule of the invention for delivery to the patient. It will be appreciated that he overall daily dose with an aerosol will vary from patient to patient, and may be administered in a single dose or, more usually, in divided doses throughout the day.

Alternatively, the molecules, medicaments and pharmaceutical compositions of the invention can be administered in the form of a suppository or pessary, or they may be applied topically in the form of a lotion, solution, cream, gel, ointment or dusting powder. The molecules, medicaments and pharmaceutical compositions of the invention may also be transdermally administered, for example, by the use of a skin patch. They may also be administered by the ocular route, particularly for treating diseases of the eye.

For ophthalmic use, the molecules, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the molecules, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the molecules, medicaments and pharmaceutical compositions of the invention agents of the invention is the preferred route, being the most convenient.

For veterinary use, the molecules, medicaments and pharmaceutical compositions of the invention is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. Advantageously, the formulation is a veterinary formulation.

Preferably, the pharmaceutical composition is for use in preventing or treating a non-cancerous condition.

In a further aspect, the invention provides a method of preventing and/or treating a non-cancerous condition or a cancerous condition in a patient comprising the step of administering to a patient in need thereof an effective amount of a peptide molecule according to the invention or a nucleic acid molecule according to the invention, or a pharmaceutical composition according to the invention.

By "therapeutically effective amount" or "effective amount" we mean an amount of a peptide molecule according to the invention or a nucleic acid molecule according to the invention, that when administered to the subject either alone or in combination with another agent, ameliorates a symptom of the disease, disorder, or condition.

By "autoimmune disease" we include the meaning of cases where it can be shown that the autoimmune process contributes to the pathogenesis of a disease. Such diseases are typically associated with a T helper lymphocyte-1 (Th-1) type immune response.

By "allergic conditions" we include the meaning of conditions associated with a T helper lymphocyte-2 (Th-2) type immune response. In allergic reaction, high IgE levels occur and Th-2 immune responses predominate over Th-1 responses, resulting in inflammatory response. Examples of allergic conditions include the following: asthma, rhinitis/hay fever, eczema and anaphylaxis.

By "adjuvant" we mean any substance which, when incorporated into or administered simultaneously with antigen, potentiates the immune response.

Typically, the non-cancerous condition is selected from the group comprising or consisting of: autoimmune disorders, such as haemolytic anaemia, thrombocytopenia, thyroiditis, pernicious anaemia, Addison's disease, autoimmune diabetes, myasthenia gravis, rheumatoid arthritis, systemic lupus erythematosus, atherosclerosis, and autoimmune encephalitis; allergic conditions such as eczema, dermatitis, allergic rhinitis, allergic conjunctivitis; allergic airways diseases; hyper-eosinophilic syndrome; contact dermatitis, food allergy; and respiratory diseases characterized by eosinophilic airway inflammation and airway hyper-responsiveness, such as allergic asthma, intrinsic asthma, allergic bronchopulmonary aspergillosis, eosinophilic pneumonia, allergic bronchitis bronchiectasis, occupational asthma, reactive airway disease syndrome, interstitial lung disease, hyper-eosinophilic syndrome, parasitic lung disease.

Further examples of autoimmune conditions are, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein (or antagonists thereof, including antibodies) of the present invention may also to be useful in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems. Other conditions, in which immune suppression is desired (including, for example, organ transplantation), may also be treatable using a protein (or antagonists thereof) of the present invention. The therapeutic effects of the polypeptides or antagonists thereof on allergic reactions can be evaluated by in vivo animals models such as the cumulative contact enhancement test (Lastbom et al., *Toxicology* 125: 59-66, 1998), skin prick test (Hoffmann et al., *Allergy* 54: 446-54, 1999), guinea pig skin sensitization test (Vohr et al., *Arch. Toxocol.* 73: 501-9), and murine local lymph node assay (Kimber et al., *J. Toxicol. Environ. Health* 53: 563-79).

Suitable assays for thymocyte or splenocyte cytotoxicity include, without limitation, those described in: Current Protocols in Immunology, Ed by J. E. Coligan et al., Strober, Pub. Greene Publishing Associates and Wiley-Interscience (Chapter 3, In vitro assays for Mouse Lymphocyte Function 3.1-3.19; Chapter 7, Immunologic studies in Humans); Herrmann et al., *Proc. Natl. Acad. Sci. USA* 78:2488-2492, 1981; Herrmann et al., *J. Immunol.* 128:1968-1974, 1982; Handa et al., *J. Immunol.* 135:1564-1572, 1985; Takai et al., I. Immunol. 137:3494-3500, 1986; Takai et al., *J. Immunol.* 140:508-512, 1988; Bowman et al., *J. Virology* 61:1992-1998; Bertagnolli et al., *Cellular Immunology* 133:327-341, 1991; Brown et al., *J. Immunol.* 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J. Immunol.* 144:3028-3033, 1990; and Assays for B cell function: In vitro antibody production, Mond, J. J. and Brunswick, M. In Current Protocols in Immunology. J. E. Coligan et al., eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan et al., Pub. Greene Publishing Associates and Wiley-Interscience (Chapter 3, In vitro assays for Mouse Lymphocyte Function 3.1-3.19; Chapter 7, Immunologic studies in Humans); Takai et al., *J. Immunol.* 137:3494-3500, 1986; Takai et al., *J. Immunol.* 140:508-512, 1988; Bertagnolli et al., *J. Immunol.* 149:3778-3783, 1992.

Dendritic cell-dependent assays (which will identify, among others, proteins expressed by dendritic cells that activate naive T-cells) include, without limitation, those described in: Guery et al., *J. Immunol.* 134:536-544, 1995; Inaba et al., *J. Experimental Medicine* 173:549-559, 1991; Macatonia et al., *J. Immunol.* 154:5071-5079, 1995; Porgador et al., *J. Experimental Medicine* 182:255-260, 1995; Nair et al., *J. Virology* 67:4062-4069, 1993; Huang et al., *Science* 264:961-965, 1994; Macatonia et al., *J. Experimental Medicine* 169:1255-1264, 1989; Bhardwaj et al., *J. Clinical Investigation* 94:797-807, 1994; and Inaba et al., *J. Experimental Medicine* 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795-808, 1992; Gorczyca et al., *Leukemia* 7:659-670, 1993; Gorczyca et al., *Cancer Research* 53:1945-1951, 1993; Itoh et al., *Cell* 66:233-243, 1991; Zacharchuk, *J. Immunol.* 145:4037-4045, 1990; Zamai et al., *Cytometry* 14:891-897, 1993; Gorczyca et al., *Int. J. Oncol.* 1:639-648, 1992.

Assays for proteins that influence early steps of T-cell commitment and development include, without limitation, those described in: Antica et al., *Blood* 84:111-117, 1994; Fine et al., *Cellular Immunology* 155:111-122, 1994; Galy at al., *Blood* 85:2770-2778, 1995; Toki et al., *Proc. Natl. Acad Sci. USA* 88:7548-7551, 1991.

Compositions of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Compositions with such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Compositions of the invention may also be useful to treat anaphylaxis and hypersensitivity to an antigenic substance or material. Compositions of this invention may be utilized to prevent or treat conditions such as, but not limited to, sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections.

In a preferred embodiment, the non-cancerous condition is asthma; alternatively, the non-cancerous condition is arthritis.

The immunosuppressive effects of the compositions of the invention against rheumatoid arthritis is determined in an experimental animal model system. The experimental model system is adjuvant induced arthritis in rats, and the protocol is described by J. Holoshitz, et al., 1983, Science, 219:56, or by B. Waksman et al., 1963, Int. Arch. Allergy Appl. Immunol., 23:129. Induction of the disease can be caused by a single injection, generally intradermally, of a suspension of killed *Mycobacterium tuberculosis* in complete Freund's adjuvant (CFA). The route of injection can vary, but rats may be injected at the base of the tail with an adjuvant mixture. The polypeptide is administered in phosphate buffered solution (PBS) at a dose of about 1-5 mg/kg. The control consists of administering PBS only.

The procedure for testing the effects of the test compound would consist of intradermally injecting killed *Mycobacterium tuberculosis* in CFA followed by immediately administering the test compound and subsequent treatment every other day until day 24. At 14, 15, 18, 20, 22, and 24 days after injection of *Mycobacterium* CFA, an overall arthritis score may be obtained as described by J. Holoskitz above. An analysis of the data would reveal that the test compound would have a dramatic affect on the swelling of the joints as measured by a decrease of the arthritis score.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., *J. Natl. Can. Inst.*, 52: 921-30 (1974), mobility and invasive potential of tumor cells in Boyden Chamber assays as described in Pilkington et al., *Anticancer Res.*, 17: 4107-9 (1997), and angiogenesis assays such as induction of vascularization of the chick chorioallantoic membrane or induction of vascular endothelial cell migration as described in Ribatta et al., *Intl. J. Dev. Biol.*, 40: 1189-97 (1999) and Li et al., *Clin. Exp. Metastasis,* 17:423-9 (1999), respectively. Suitable tumor cells lines are available, e.g. from American Type Tissue Culture Collection catalogs.

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, *Medicine,* 2d Ed., J. B. Lippincott Co., Philadelphia).

In a further aspect, the invention provides a peptide molecule according to the invention or a nucleic acid molecule according to the invention for use in the relief of pain.

In a further aspect, the invention provides a pharmaceutical composition which is for use in the relief of pain. Preferred pharmaceutical compositions according to the invention are described above and in the accompanying examples.

In a further aspect, the invention provides the use of a peptide molecule according to the invention or a nucleic acid molecule according to the invention in the manufacture of a medicament for the relief of pain.

By "use in the relief of pain" we include any treatment which influences the pain felt by an individual, such influence including a delay in the onset, a reduction in the severity, a reduction of the duration, and/or the removal of the feeling of pain. (and/or analgesia and/or hyperanalgesia) in a human or animal patient. By "pain" we also include analgesia and/or hyperanalgesia—by "hyperalgesia" we mean an earlier onset, an increase in the severity, an increase of the duration, and/or increased susceptibility to the feeling of pain.

In a preferred embodiment, the medicament further comprises at least one additive for assisting or augmenting the action of the peptide molecule or nucleic acid molecule. Typically, the additive is selected from at least one of paracetamol, aspirin, ibuprofen, other non-steroidal anti-inflammatory drugs (NSAIDS), cylooxygenase-2-selective inhibitors (CSIs), opiates.

By "additive" we include an ingredient that is provided in addition to the main medicament and that is pharmacologically active either independently or in combination with the main medicament, whereby its presence in the medicament assists or augments the action of the main medicament.

Preferably, the medicament provides prolonged or sustained pain relief.

Advantageously, in the use according to the invention, the daily dosage level will be from 0.0001 to 100,000 mg, administered in single or divided doses; preferably, the daily dosage level is 0.0001 to 1000 mg.

Preferred pharmaceutical formulations include those in which the active ingredient is present in at least 1% (such as at least 10%, preferably in at least 30% and most preferably in at least 50%) by weight. That is, the ratio of active ingredient to the other components (i.e, the addition of adjuvant, diluent and carrier) of the pharmaceutical composition is at least 1:99 (e.g. at least 10:90, preferably at least 30:70 and most preferably at least 50:50) by weight.

Typically, the time between dose administration to the patient is between six and twelve hours; in a preferred embodiment, the time between dose administration to the patient is between nine and twelve hours after the previous dose; more preferably, the time between dose administration to the patient is between twelve hours and twelve days; even more preferably, the time between dose administration to the patient is between twelve days and six months.

In a preferred embodiment, the invention provides a use wherein the medicament of the invention is used to relieve pain in a human or animal patient.

Preferably, the pharmaceutical composition or the medicament of the invention is formulated to permit administration by at least one route selected from the group comprising or consisting of: intranasal; oral; parenteral; topical; ophthalmic; suppository; pessary; or inhalation routes. Formulations suitable for such administration routes are well known to those in the art of pharmacy and medicine and exemplary formulations are described above and in the accompanying examples.

Preferably, the pain is selected from the group comprising or consisting of: backache; headache; toothache; earache; arthritis; gout; soft tissue trauma; ligament and/or tendon traumatic damage; broken bones; cancer; post-operative pain; menstrual pain; obstetric pain; renal tract pain; visceral pain; burns; abscesses; and other infections.

In a further aspect, the invention provides a method of relieving pain in a patient comprising the step of administering to a patient in need thereof an effective amount of a peptide molecule of the invention and/or a nucleic acid molecule of the invention and/or pharmaceutical composition of the invention.

In a further aspect, the invention provides the use of a peptide molecule according to the invention and/or a nucleic acid molecule according to the invention as an adjuvant.

In a further aspect, the invention provides an adjuvant system comprising (i) a peptide molecule according to the invention and/or a nucleic acid molecule according to the invention and (ii) an antigen.

Preferably, the antigen is selected from the group comprising or consisting of: anthrax antigen; cholera antigen; diphtheria antigen; *haemophilus influenza* b (Hib) antigen; hepatitis A antigen; hepatitis B antigen; influenza antigen; Japanese encephalitis antigen; measles, mumps and rubella (MMR) antigen; meningococcal antigen; pertussis antigen; pneumococcal antigen; poliomyelitis antigen; rabies antigen; rubella antigen; smallpox and/or vaccinia antigen; tetanus antigen; tick-borne encephalitis antigen; tuberculosis antigen; typhoid antigen; varicella/herpes zoster antigen; yellow fever antigen; and veterinary vaccine antigen.

In a further aspect, the invention provides a method of stimulating cytokine production in a cell comprising the step of administering a peptide molecule according to the invention or a nucleic acid molecule according to the invention.

Preferably, cytokine production is increased at least 10-fold relative to normal levels.

Normal levels for a particular cell type can be readily determined using a control sample that is not exposed to the polypeptide or polynucleotide of the invention in any of the assays discussed below or as described in the examples.

A polypeptide of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DAIG, T10, B9, B9/11, BaF3, MC9/G, M+(preB M+), 2E8, RBS, DA1, 123, T1165, HT2, CTLL2, TF-1, Mo7e, CMK, HUVEC, and Caco.

Assays for T-cell or thymocyte proliferation include without limitation those described in: Current Protocols in Immunology, Ed by J. E. Coligan et al., Pub. Greene Publishing Associates and Wiley-Interscience (Chapter 3, In vitro assays for Mouse Lymphocyte Function 3.1-3.19; Chapter 7, Immunologic studies in Humans); Takai et al., *J. Immunol.* 137: 3494-3500, 1986; Bertagnolli et al., *J. Immunol.* 145:1706-1712, 1990; Bertagnolli et al., Cellular Immunology 133: 327-341, 1991; Bertagnolli, et al., *I. Immunol.* 149:3778-3783, 1992; Bowman et al., *I Immunol.* 152:1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. Coligan eds. Vol 1 pp. 3.12.1-3.12.14, John Wiley and Sons, Toronto. 1994; and Measurement of mouse and human interleukin-γ, Schreiber, R. D. In Current Protocols in Immunology. J. E. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S, and Lipsky, P. E. In Current Protocols in Immunology. J. E. Coligan eds. Vol 1 pp. 6.3.1-6.3.12, John Wiley and Sons, Toronto. 1991; deVries et al., *J. Exp. Med.* 173:1205-1211, 1991; Moreau et al., *Nature* 336:690-692, 1988; Greenberger et al., *Proc. Natl. Acad. Sci. USA* 80:2931-2938, 1983; Measurement of mouse and human interleukin 6—Nordan, R. In Current Protocols in Immunology. J. E. Coligan eds. Vol 1 pp. 6.6.1-6.6.5, John Wiley and Sons, Toronto. 1991; Smith et al., *Proc. Natl. Acad. Sci. U.S.A.* 83:1857-1861, 1986; Measurement of human Interleukin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In vitro assays for Mouse Lymphocyte Function; Chapter 6, Cytokines and their cellular receptors; Chapter 7, Immunologic studies in Humans); Weinberger et al., *Proc. Natl. Acad. Sci. USA* 77:6091-6095, 1980; Weinberger et al., *Eur. J. Immun.* 11:405-411, 1981; Takai et al., *J. Immunol.* 137:3494-3500, 1986; Takai et al., *J. Immunol.* 140:508-512, 1988.

In a preferred embodiment, the cytokine is selected from the group comprising or consisting of: IL-1β; IL-2; IL-6; IL-8; IL-10; IL-12; TNF-α; Interferon-γ; GM-CSF.

The invention further provides a method of assessing the presence and/or amount in a sample of a peptide molecule according to the invention or a nucleic acid molecule according to the invention comprising or consisting of the steps of:
  i) providing a test sample;
  ii) contacting the test sample with a cell;

iii) measuring and/or detecting the level of production of one or more cytokine by the cell;

iv) comparing the level of production of one or more cytokine in (iii) with the level of production of the one or more cytokine in a control sample wherein a higher level of production of one or more cytokine induced by the test sample compared to the control sample indicates the presence and/or amount in the test sample of a peptide molecule according to the invention or a nucleic acid molecule according to the invention.

Figure 25:
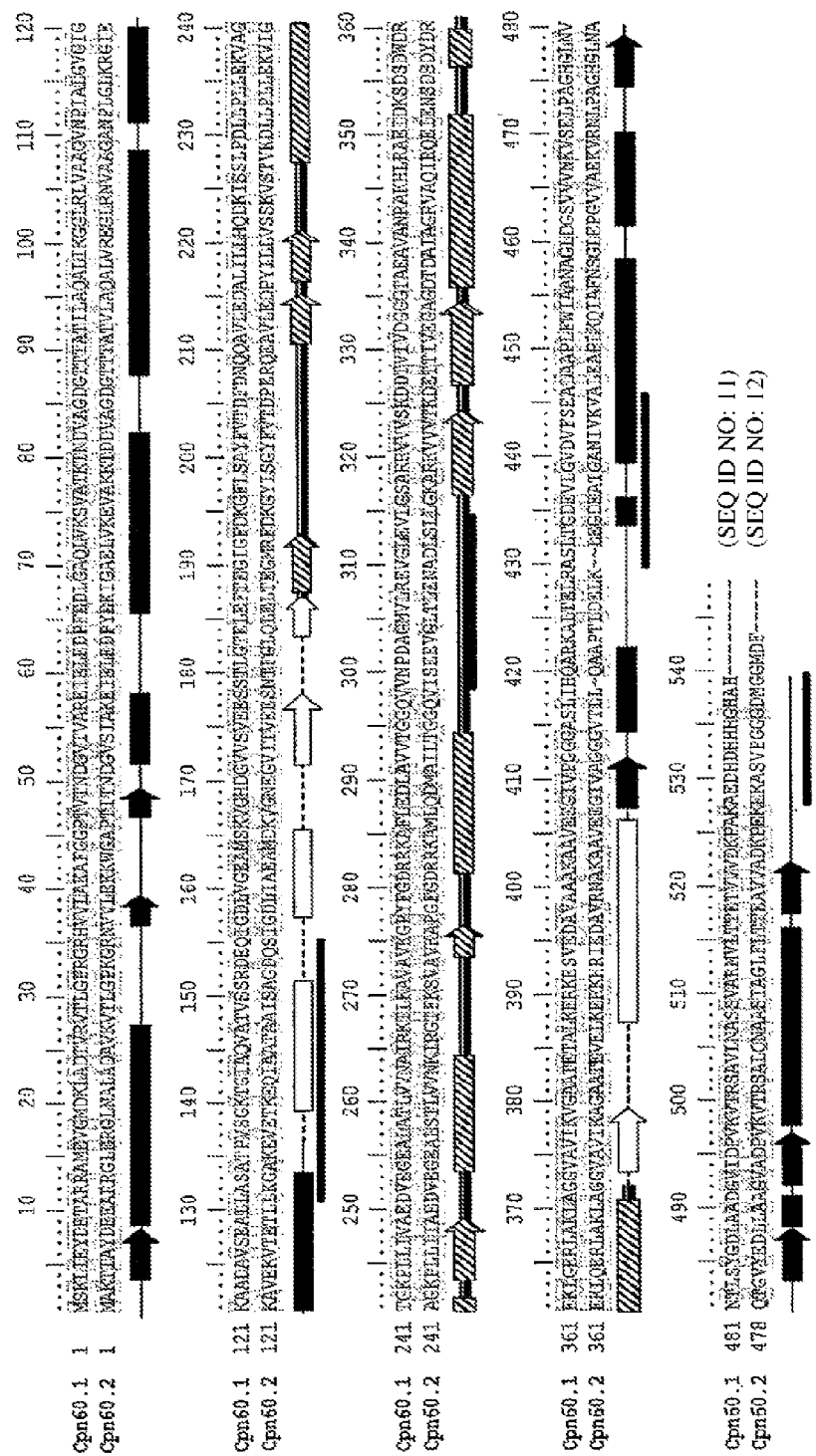

"MT60.1", "Mtcpn60.1", "cpn 60.1", "60.1" and "chaperonin 60.1" are used interchangeably throughout the specification to refer to the amino acid sequence shown in FIG. 25.

The listing or discussion of an apparently prior-published document in this specification should not necessarily be taken as an acknowledgement that the document is part of the states of the art or is common general knowledge.

Preferred, non-limiting examples which embody certain aspects of the invention will now be described, with reference to the following figures:

FIG. 1. The recruitment of eosinophils to the airways 24 h after repeated ovalbumin challenged was inhibited in mice treated with Cpn60.1, Cpn10 but not Cpn60.2. Vertical lines represent standard error of mean (SEM) of 4-12 (Cpn60.1), 3-5 (Cpn60.2), 4-10 (Cpn10) animals per group. *Significant reduction in percentage of eosinophils compared with ovalbumin alone.

Figure 2:
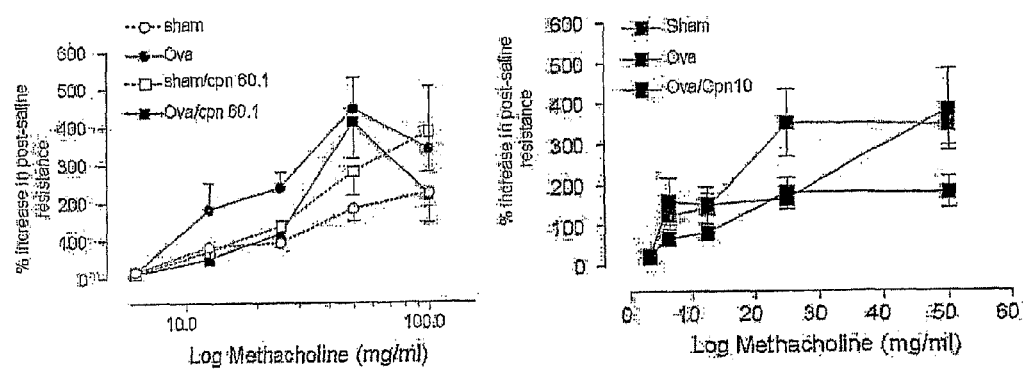

FIG. 2. The Bronchial hyper-responsiveness to methacholine 24 h after repeated ovalbumin challenged was reduced in mice treated with Cpn60.1, Cpn10 but not Cpn60.2 (n=16-17). Vertical lines represent SEM.

Figure 3:
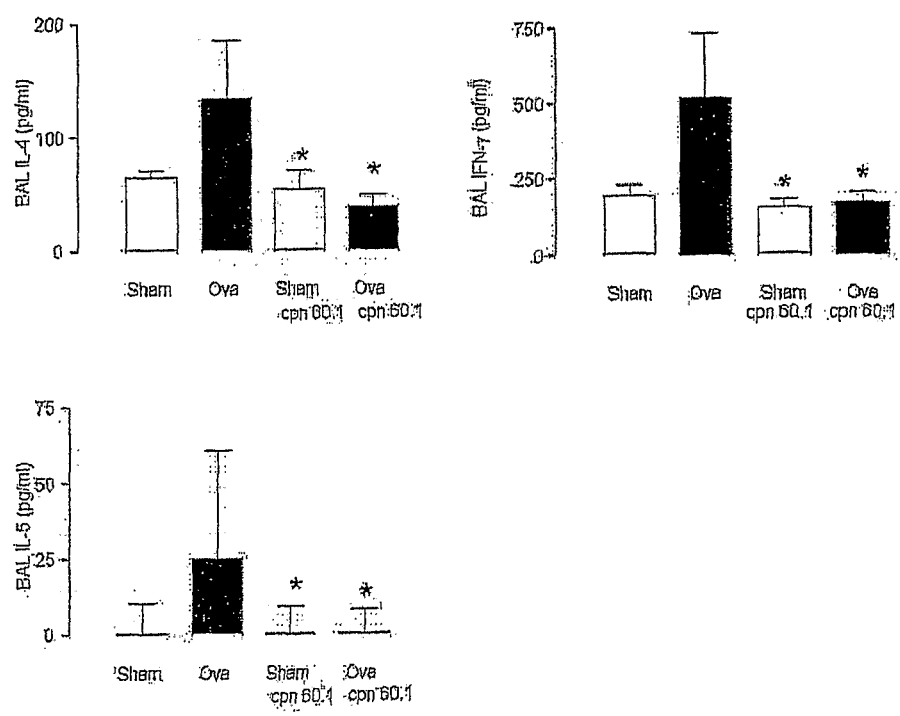

FIG. 3. The levels of cytokines in BAL fluid 24 h after repeated ovalbumin challenge was inhibited in mice treated with Cpn60.1. Vertical lines represent SEM. * Significant reduction in levels of cytokines compared with ovalbumin alone (n=8-10).

Figure 4:
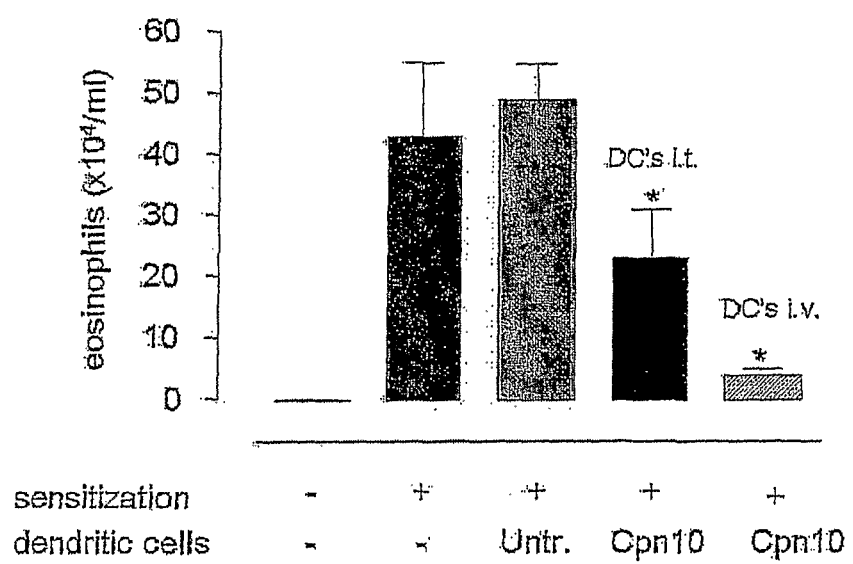

FIG. 4. Transfer of Cpn10 pre-treated dendritic cells (10 μg/ml) in vitro to OVA-sensitized recipient mice significantly inhibited eosinophils migration to the lung Vertical lines represent SEM. * Significant reduction in number of eosinophils compared with sensitized mice instillated with untreated DC's (n=9-15).

Figure 5:
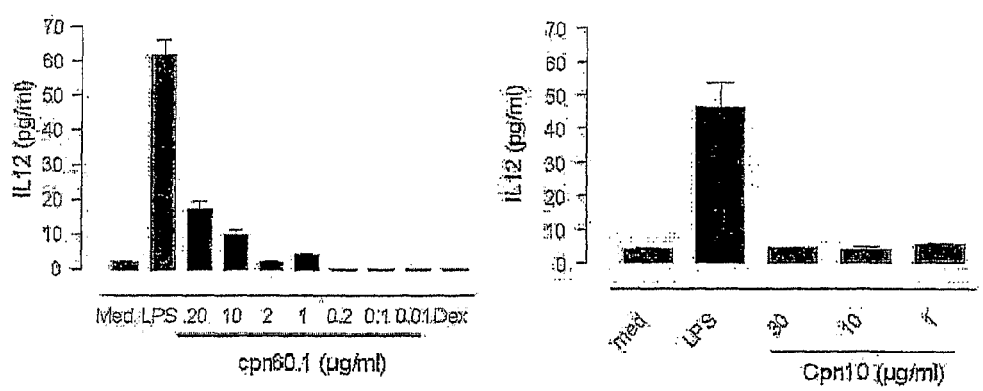

FIG. 5. Dendritic cells pulsed with Cpn60.1 for 48 hours produced IL12 in a dose-dependant manner. Pre-treatment of dendritic cells with Cpn10 (10 μg/ml) induced low levels of 102. Cells were stimulated with the chaperonins for 48 h and tested in quadruplicate and each column represents the mean of two experiments. Vertical lines represent Standard Deviation (SD).

Figure 6:
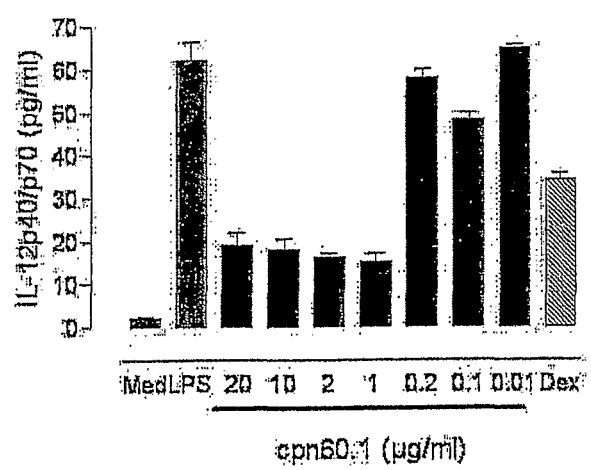

FIG. 6. Pre-incubation of dendritic cells with Cpn60.1 for 24 hours inhibit IL12 production induced by LPS. Cells were stimulated with the chaperonins for 248 h and with LPS for further 24 h. All concentrations were tested in quadruplicate and each column represents the mean of two experiments. Vertical lines represent SD.

Figure 7:
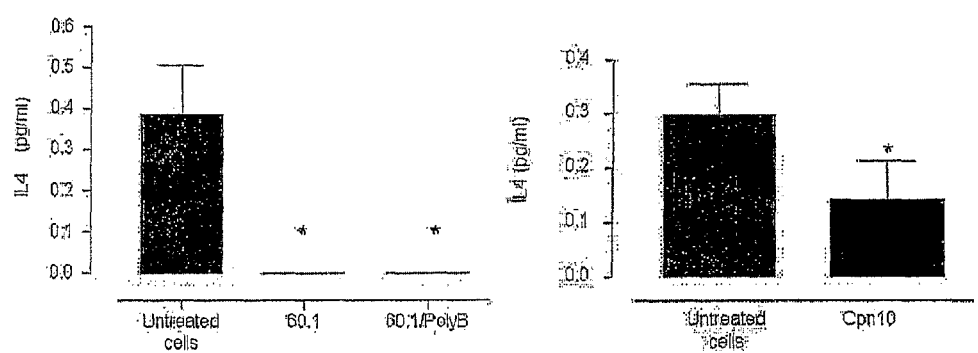

FIG. 7. Pre-treatment of dendritic cells with Cpn60.1 or Cpn10 (10 μg/ml) suppressed the levels of IL4 in a co-culture of dendritic cells and RD11.10 T cells. IL5 and IL10 were not detected in this culture. Dendritic cells were stimulated with the chaperonins for 24 h before co-culturing them with D0.11 cells. The co-culture was maintained for 6 days and cells were stimulated with anti-CD3 and anti-CD28 for further 24 hours. Supernatants were collected and tested in quadruplicate. Vertical lines represent SD.

Figure 8:
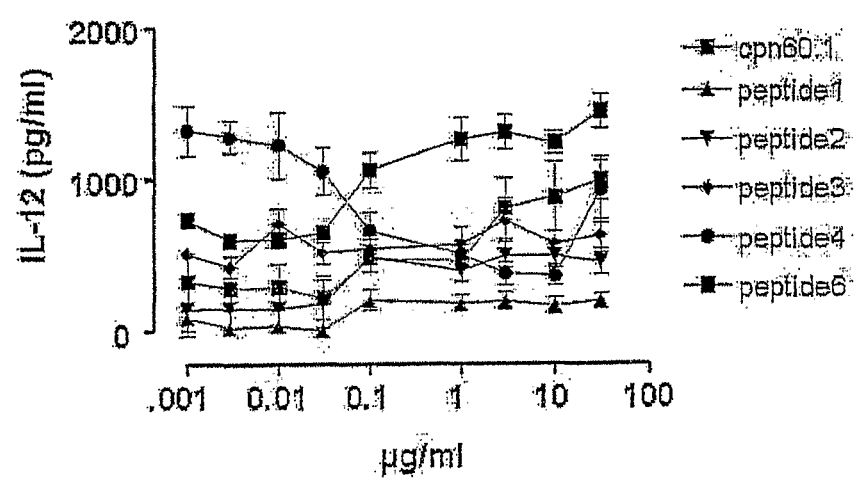

FIG. 8. Pre-treatment of spleen cells of C57131/6 mice with various concentrations of Cpn60.1 and its peptides induce IL-12 release in vitro. Medium contained 5 μg/ml of polymixin B. Cells were stimulated with the chaperonins for 24 h and supernatants were tested in quadruplicate. Each line represents the mean of two experiments.

Figure 9:
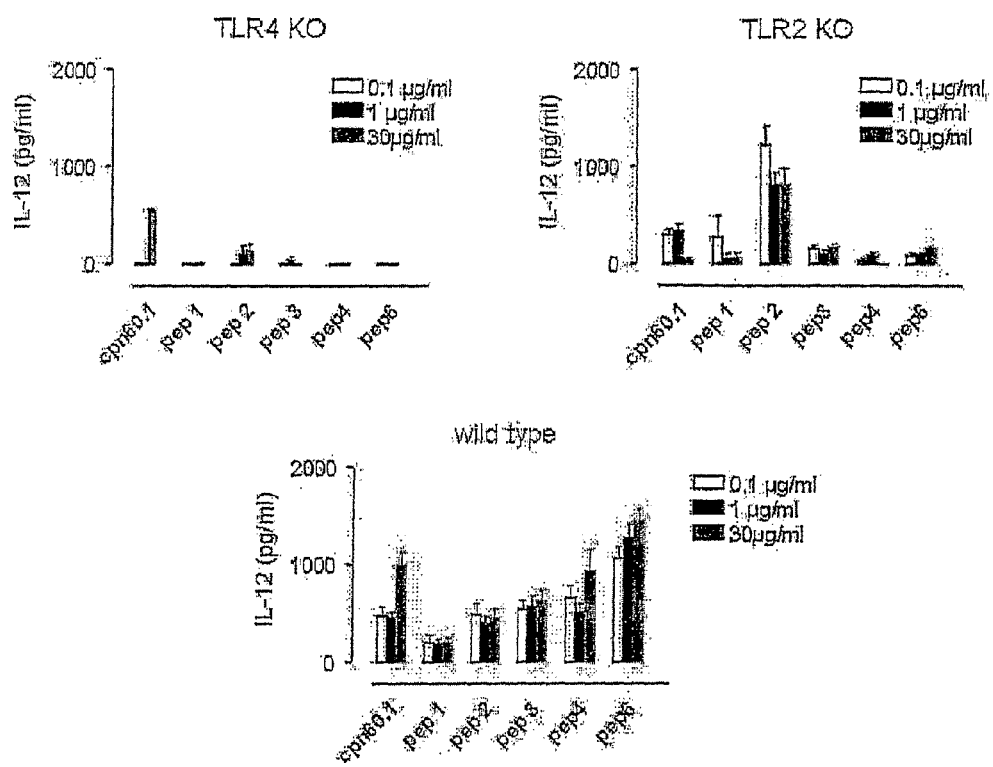

FIG. 9. Spleen cells collected from TLR4KO mice presented a reduced response to the chaperonin 60.1 and its peptides when compared to their wild type counterpart C57b1/6 mice. TLR2KO mice also presented an inhibited response to the chaperonins. All concentrations were tested in quadruplicate. Vertical lines represent SD.

Figure 10:
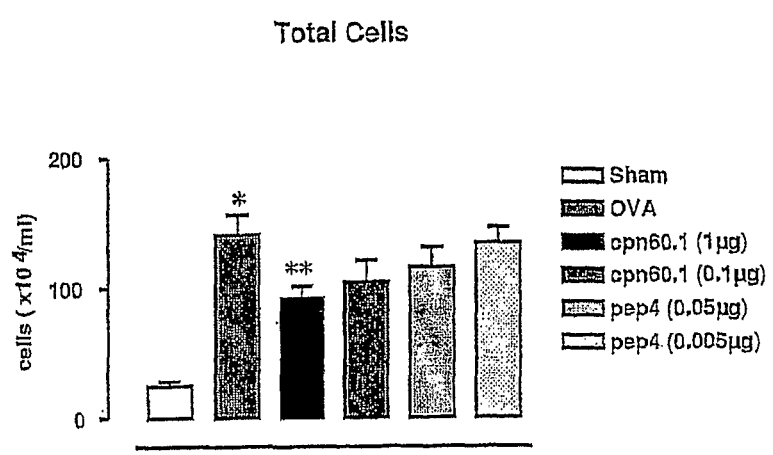

FIG. 10. The recruitment of total cells to the airways 24 h after repeated ovalbumin challenged was inhibited in mice treated with Cpn60 and Cpn60.1-peptide 4. Vertical lines represent SEM of 5-9 animals per group. * Significant reduction in number of total cells compared to sham group. **Significant reduction in number of total cells compared with ovalbumin alone.

Figure 11:
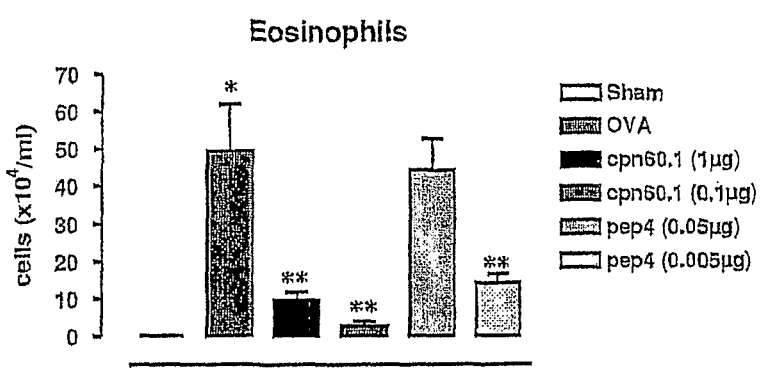

FIG. 11. The recruitment of eosinophils to the airways 24 h after repeated ovalbumin challenged was inhibited in mice treated with Cpn60 and Cpn60.1-peptide 4. Vertical lines represent SEM of 5-9 animals per group. *Significant reduction in number of eosinophils compared to sham group. **Significant reduction in number of eosinophils compared with ovalbumin alone.

Figure 12:
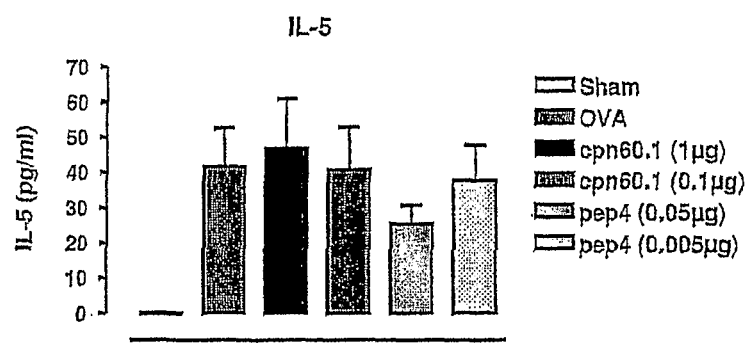

FIG. 12. The levels of IL-5 in BAL fluid 24 h after repeated ovalbumin challenge was not significantly inhibited in mice treated with Cpn60.1 or Cpn60.1-peptide 4. Vertical lines represent SEM.

Figure 13:
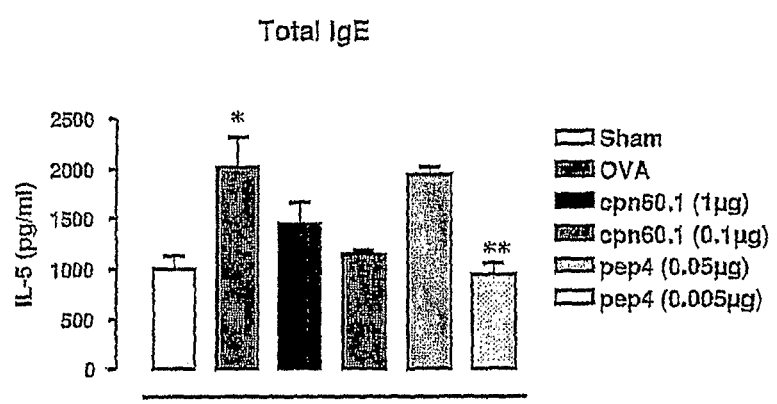

FIG. 13. The levels of total IgE circulating in serum 24 h after repeated ovalbumin challenge was significantly inhibited in mice treated with Cpn60.1-peptide 4 (0.005 μg/mouse). Vertical lines represent SEM. ** Significant increase in levels of total IgE compared to ovalbumin alone.

Figure 14:
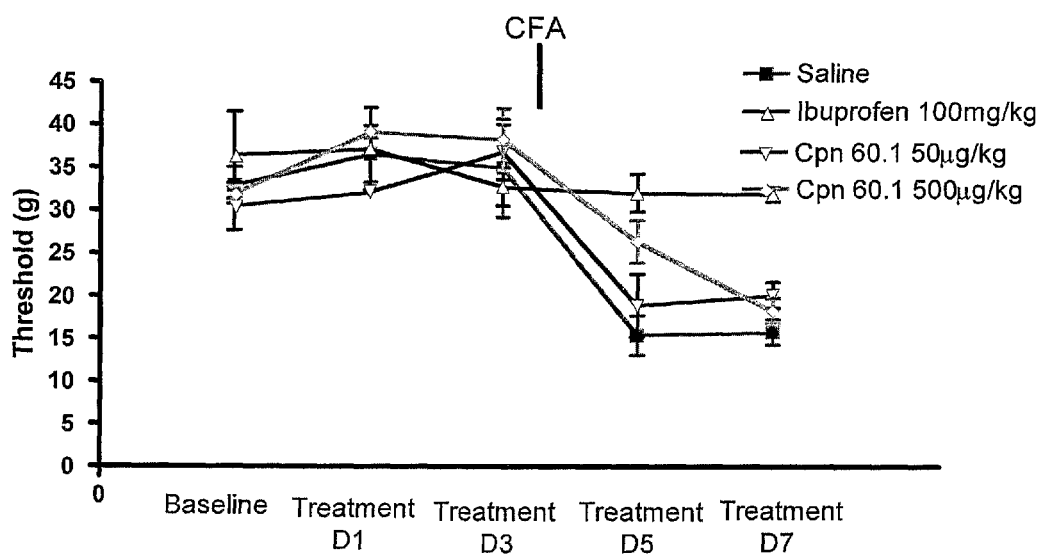

FIG. 14. Effect of Cpn60.1 on mechanical hyperalgesia in CFA-treated rats (n=6).

Figure 15:
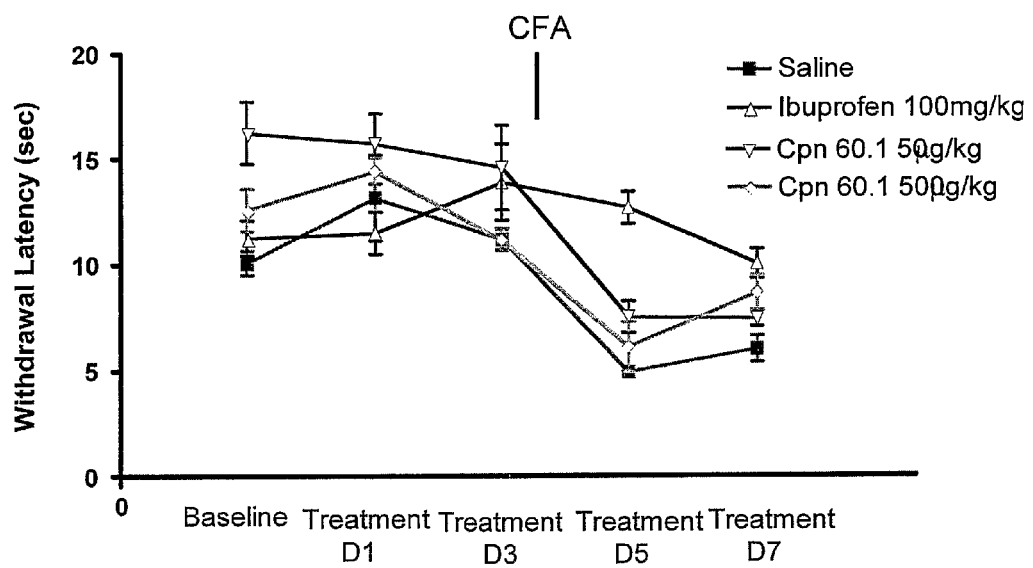

FIG. 15. Effect of Cpn60.1 on thermal hyperalgesia in CFA-treated rats (n=6).

Figure 16:
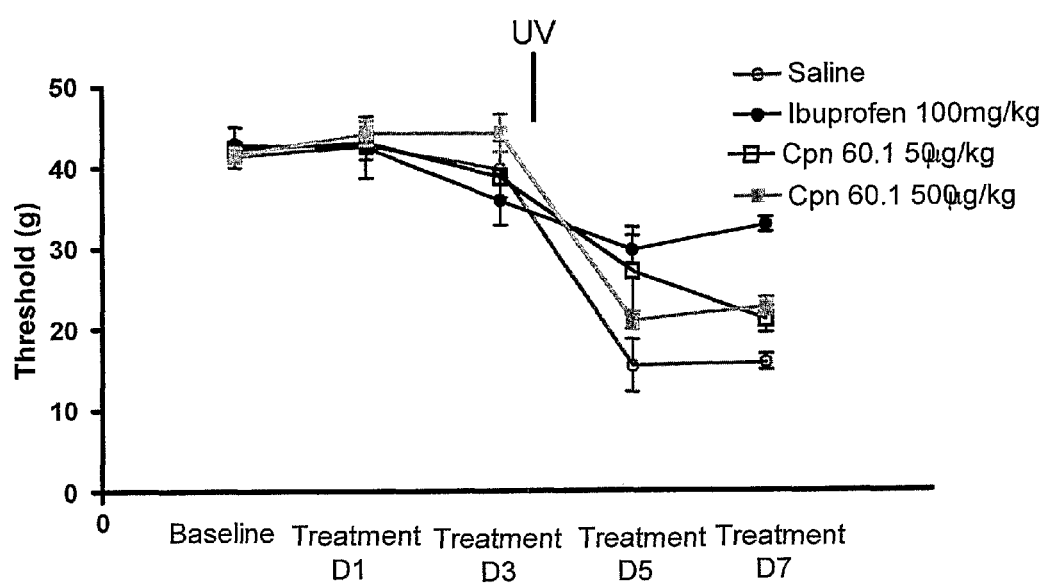

FIG. 16. Effect of Cpn60.1 on mechanical hyperalgesia in UV-treated rats (n=6).

Figure 17:
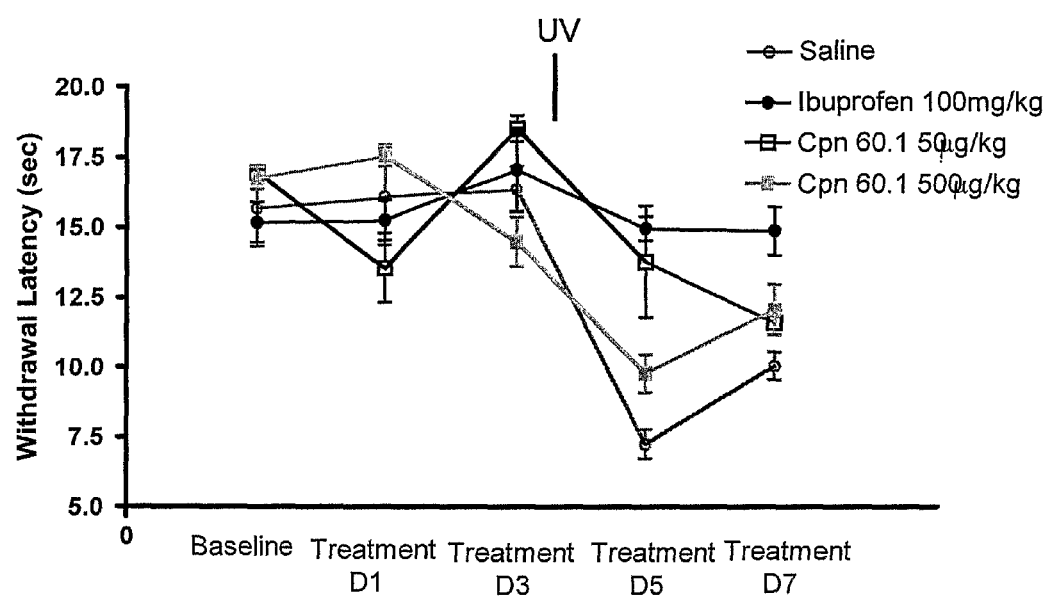

FIG. 17. Effect of Cpn60.1 on thermal hyperalgesia in UV-treated rats (n=6).

Figure 18:
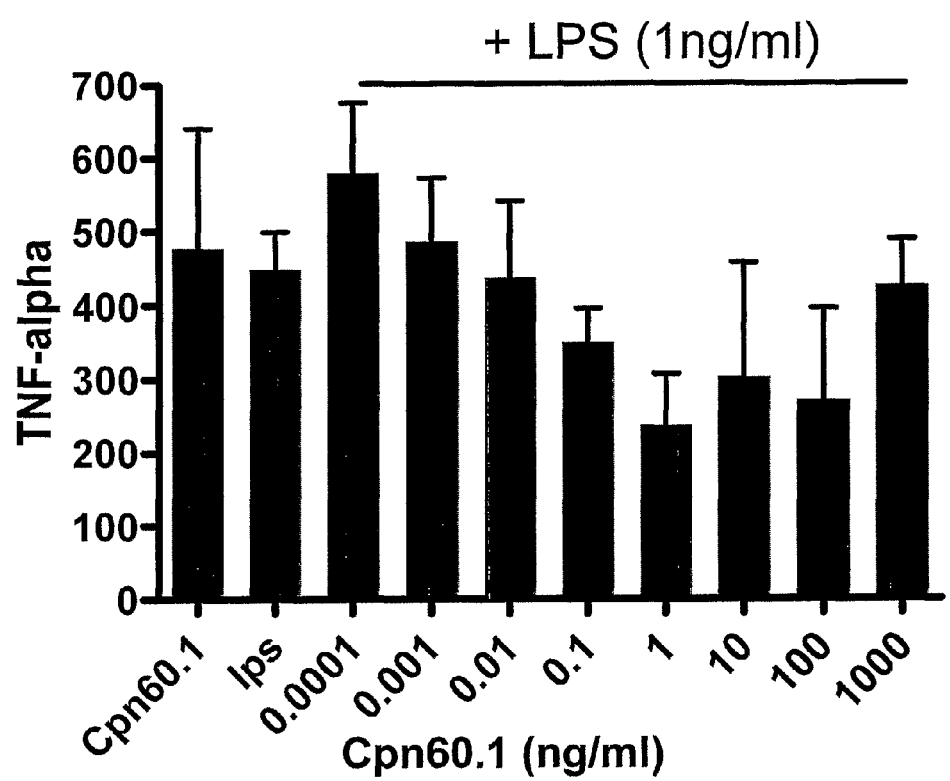

FIG. 18. Pre-treatment of human peripheral blood monocytes with Cpn60.1 suppresses LPS-induced TNF-alpha secretion. Data shows an attenuation of TNF-α secretion with increasing concentration of Cpn60.1. Maximum inhibition at 1 ng/ml although not significant. Data represented as mean±SEM (n=5).

Figure 19:
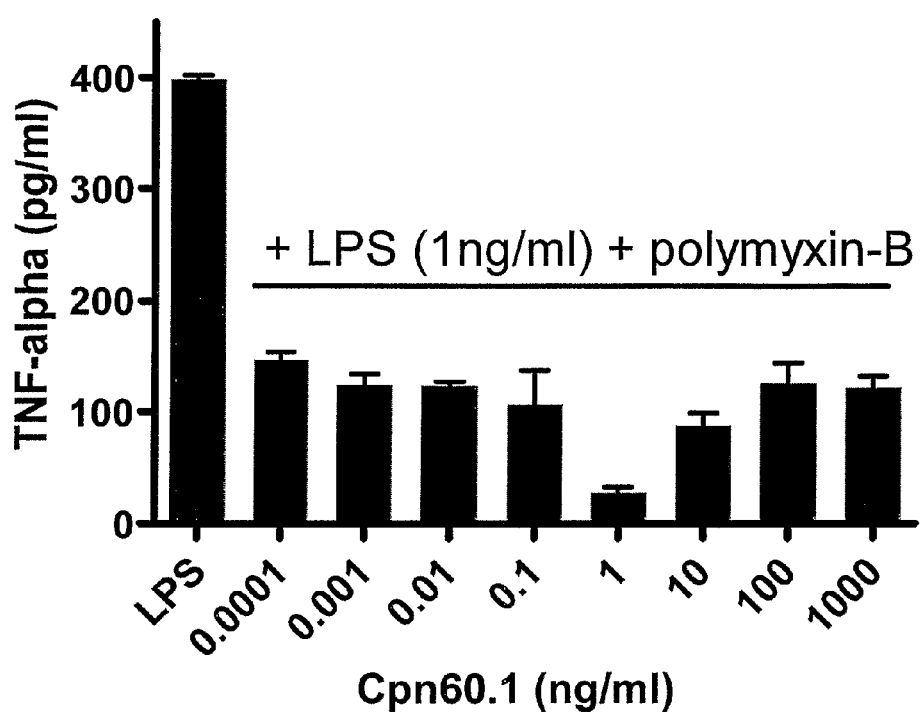

FIG. 19. Pre-treatment of human peripheral blood monocytes with Cpn60.1 suppresses LPS-induced TNF-alpha secretion in the presence of polymyxin-B. Data shows an attenuation of TNF-α secretion with increasing concentration of Cpn60.1. Maximum inhibition at Mg/ml. Data represented as mean±SEM (n=5).

Figure 20:
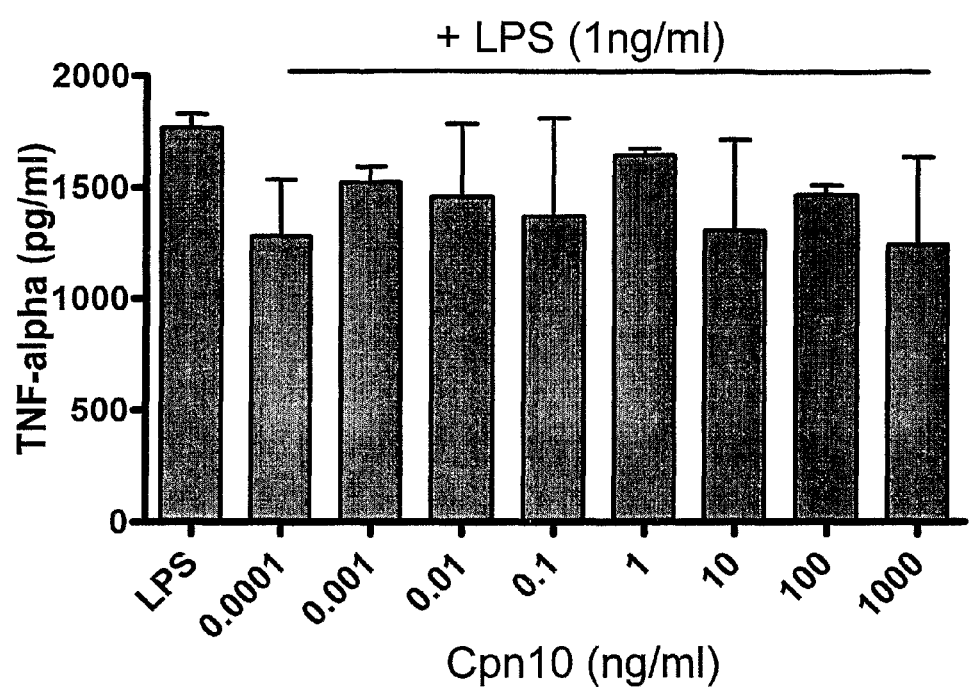

FIG. 20. Pre-treatment of human peripheral blood monocytes with Cpn10 does not suppress LPS-induced TNF-alpha secretion. Cpn10 had no effect at inhibiting TNF-α secretion at any concentration when compared to LPS. Data represented as mean±SEM (n=5).

Figure 21:
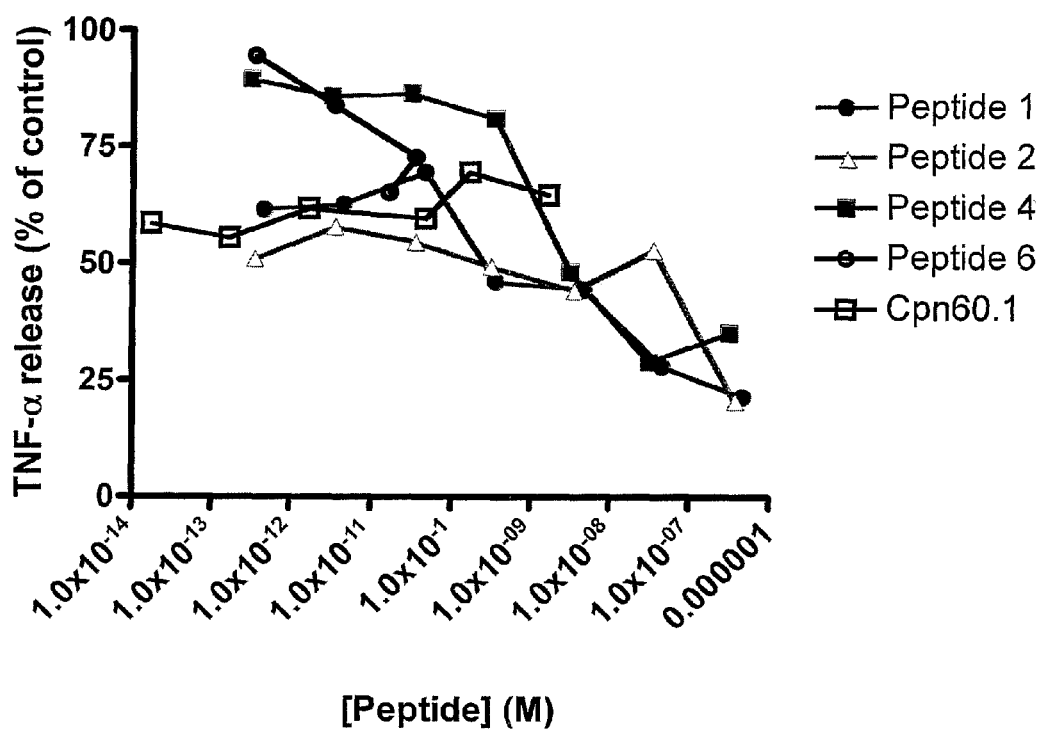

FIG. 21. Pre-treatment of human peripheral blood monocytes with Cpn60.1 or Cpn60.1 peptides suppress TNF-alpha release induced by LPS. Data are expressed as the mean of two separate experiments in triplicate expressed as a percent of control values.

Figure 22:
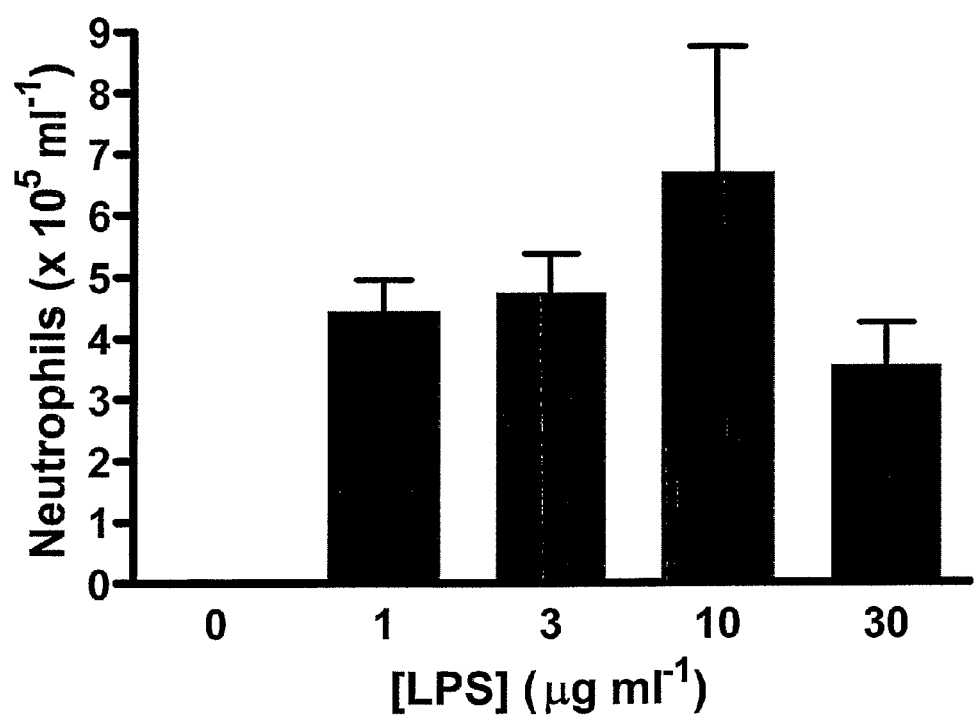

FIG. 22. Total number of neutrophils recovered from lavage of increasing concentration of LPS (1 μg/ml) vs. saline-challenged mice at 24 hours (n=4).

Figure 23:
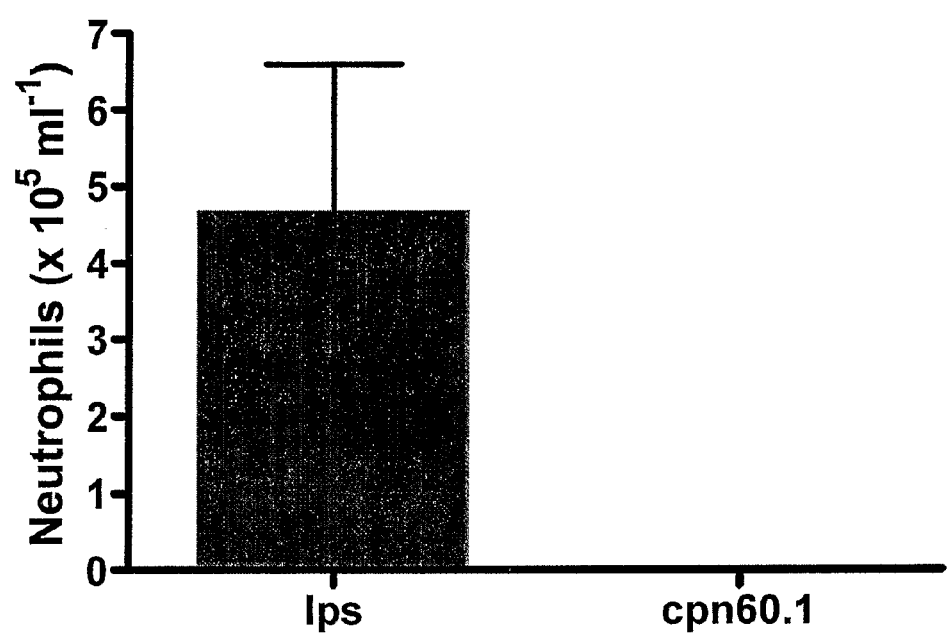

FIG. 23. Total number of neutrophils recovered from lavage of LPS-treated mice (1 µg/ml) and Cpn60.1-treated mice at 24 hours (n=4).

Figure 24:
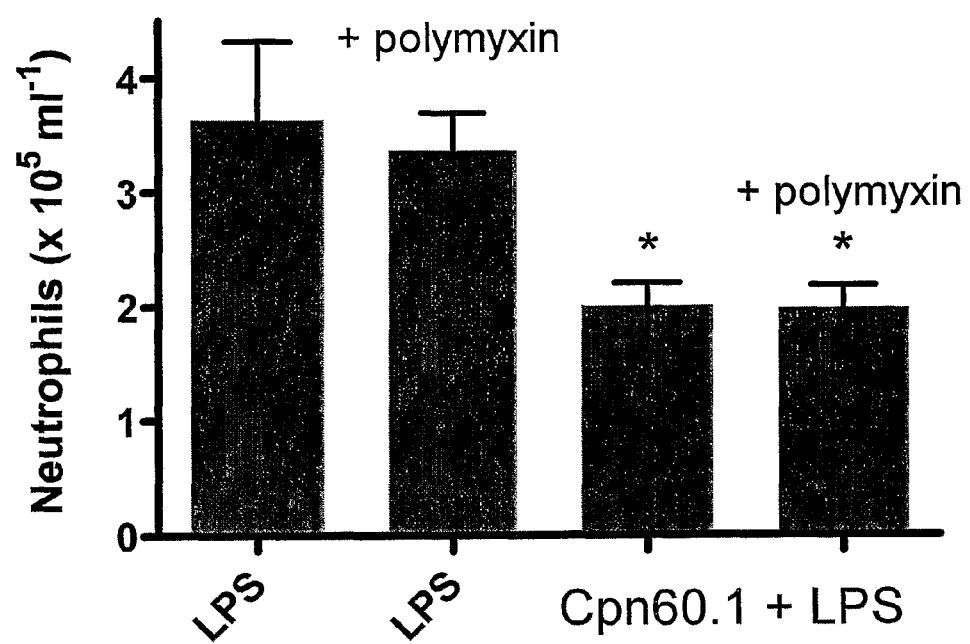

FIG. 24. Total number of neutrophils recovered from lavage of increasing concentration of LPS (1 µg/ml) vs. saline-challenged mice at 24 hours (n=4). Cpn60.1-treated animals reduced LPS-induced neutrophilia. Significantly inhibited in comparison to LPS-treated group (*p<0.05).

FIG. 25. Peptides covering the equatorial domain of *Mycobacterium. tuberculosis* Cpn60.1. The equatorial domain is marked by the solid black lines and boxes/arrows under the sequence.

Peptides 1, 2, 5, 7, 8, 9, 10 are highly surface-exposed and/or regions of high dissimilarity between Cpn60.1 and Cpn60.2 and should therefore be the potentially most interesting peptides. Peptides 3 and 9 are surface-exposed but towards the inner face of a putative oligomeric structure and are highly interesting to study. Peptide 4 and 6 are both partly buried in the structure and may be of relatively lower potential interest.

EXAMPLES

Overview of Examples

The objectives of our experiments were to investigate the anti-inflammatory properties of chaperonins in a model of allergic inflammation. The results extend our previous findings showing that both Cpn60.1 and Cpn10 inhibited allergic inflammatory responses in vivo, and at the cellular level were able to inhibit dendritic cell function which might explain the anti-inflammatory properties of these molecules in vivo.

The structural determinant of this anti-inflammatory property of Cpn60.1 remains to be established. Therefore, various peptide sequences of Cpn60.1 were investigated for potential anti-inflammatory properties in vitro and in vivo. A number of these peptides appeared to have immunomodulatory activity in vitro and anti-inflammatory properties in vivo, suggesting that the structural determinants of the activity residing within chaperonins is amenable to interrogation with the view of finding novel anti-inflammatory agents.

Example 1

Effect of Cpn60.1 and 10 in a Murine Model of Allergic Inflammation

Allergic diseases, including asthma are considered to be associated with over activity of Th2 lymphocytes, and so strategies designed to induce immune deviation may be useful in suppressing allergic inflammation in asthma. It has been shown that both *M. tuberculosis* and the vaccine *M. bovis* BCG, which is antigenically very similar to *M. tuberculosis* (Harboe M et al. *Scand J. Immunol.* 1979; 9:115-24) can suppress allergic lung inflammation. Data from Helperby Therapeutics have confirmed that *M. tuberculosis* has three chaperonins, namely 60.1, 60.2, and 10. Moreover, we have previously demonstrated that Cpn10 and 60.1 but not 60.2 suppressed lung inflammation in a murine model of asthma (Riffo-Vasquez, Y. et al., *Clin. Exp. Allergy*, 2004, 34:712-19).

Allergic inflammation in the lung is induced by 2 intraperitoneal injections of 10 µg of ovalbumin (OVA) in 1 mg of alum with 7 days interval between them. Control animals receive alum only. On day 14, all animals are exposed to an aerosol of OVA for 25 minutes, once a day for 3 consecutive days. All measurements are performed 24 h after the last antigen challenge.

We have shown that intra-tracheal administration of 10 µg of Cpn60.1 or Cpn10, 24 h before the second injection of OVA and one hour before each antigen challenge can significantly inhibit airways inflammation (FIG. 1), hyper-responsiveness (FIG. 2) and cytokine release in the lung (FIG. 3). However, the mechanism by these chaperonins exert this effect in vivo remain to be established.

Example 2

Effect of Cpn 10 and Cpn60.1 on Murine Dendritic Cells Function

It has been shown that mycobacterial heat shock proteins (hsp) can enhance antigen processing and presentation by dendritic cells (DC) of exogenous proteins to T cells, without the need of complex formation between hsp and the protein (Chen K., et al., *J. Leuk. Biol.*, 2004, 75:1-7).

In order to clarify the mechanism by which Cpn10 and 60.1 regulated allergic lung inflammation in vivo, we have investigated the effect of these chaperonins on bone marrow dendritic cell function in vitro.

Bone marrow cells from Balb/c mice were collected and cultured for 6 days in complete Dulbecco's Modified Eagle Medium containing 8 ng/ml of mouse GM-CSF. On day 6 of culture, the cells were collected, re-plated for 1 hour for removal of adherent cells, washed and plated at $2 \times 10^8$ cells/well in 6-wells plates for analysis of surface markers expression and transference experiments and at $10^5$ cells/well in 96-wells plate for cytokine measurements. In other experiments, cells were incubated at 106 cells/well for 24 h with the chaperonins and then another further 24 h with LPS (10 ng/ml).

The DC's were pre-treated in vitro for 24 h with Cpn10 (10 µg/ml) and then administrated topically to the lungs of OVA-sensitized recipient mice. This treatment significantly inhibited eosinophil migration to the lung (FIG. 4), reproducing the effect observed in vivo with the chaperonin itself.

Pre-treatment of DC in vitro with Cpn60.1 (0.1-30 µg/ml) induced the release of IL-12 in a dose dependent-manner. However, pre-treatment of DC with Cpn10 (10 µg/ml) induced lower levels of IL-12 release in comparison to LPS and Cpn60.1 (FIG. 5).

Pre-incubation of DC's with Cpn60.1 but not Cpn10 for 24 hours inhibited IL12 production induced by LPS (FIG. 6).

DC pre-treated with Cpn60.1 (10 µg/ml) or Cpn10 (10 µg/ml) for 24 h suppressed the release of IL4 from RD11.10 T cells in a DC/T cell co-culture. After 6 days of culture, cells were stimulated with anti-CD3 and anti-CD28 for further 24 hours and supernatants collected. IL5 and IL10 were not detected in this culture (FIG. 7).

Example 3

The Effect of Chaperonin 60.1 Peptides In vitro

In order to determine the structural determinants of Chaperonin 60.1 responsible for the biological actions observed we have investigated the effect of 5 different peptide sequences designated in this study as peptide 1, 2, 3, 4 and 6 in various in vitro biological assays.

The specific sequences are shown below:

| Peptide name | Peptide sequence |
|---|---|
| Peptide 1 (p60.1_30) | LGPRGRHVVLAKAFGGPTVTN (SEQ ID NO: 2) |
| Peptide 2 (p60.1_406) | EEGIVPGGGASLIHQARKALTELRASL (SEQ ID NO: 6) |
| Peptide 3 (p60.1_433) | TGDEVLGVDVFSEALAAPLFWIAANAGL (SEQ ID NO: 7) |
| Peptide 4 (p60.1_461) | DGSVVVNKVSELPAGHGLNVNTLSYGDLAAD (SEQ ID NO: 8) |
| Peptide 6 (p60.1_515) | LTTETVVVDKPAKAEDHDHHHGHAH (SEQ ID NO: 10) |

Cpn60.1 batch used in these experiments: Cpn60.1 1_04-03/1.

We have investigated the effect of these peptides in a culture of spleen cells. Spleens were collected from C57Bl/6 mice or TLR4 and TLR2KO mice. The organs were macerated in sterile conditions and cell suspension passed through a 70 μm cell strainer. Red blood cells were removed by osmotic chock with sterile water. The cells remained were washed and plated at $10^6$/well for IL-12 measurements. Cells were incubated with different concentrations of the peptides or chaperonin 60.1 (0.001-30 μg/ml). Supernatants were collected 24 h later and kept at −20° C. IL-12 was measured by conventional ELISA assay.

Our experimental observations demonstrated that Cpn60.1 and all peptides induce IL-12 release in a splenocyte culture Peptide 4 is more effective than Cpn60.1 at lower concentrations (0.001-0.1 μg/ml). However, at a higher concentration (0.1-30 μg/ml) this peptide showed a reduced effect in comparison to Cpn60.1. Peptide 6 has a similar effect at higher concentrations in comparison to Cpn60 but has a less potent effect at lower concentrations. (FIG. 8). All cultures were performed in the presence of polymixin B to rule out any effect of LPS contamination on the functional responses that were measured.

We further examined the role of toll receptors (TLR) in the response of spleen cells to these peptide sequences. Spleen cells collected from TLR4KO mice were a significantly refractory in their ability to produce IL-12 in response to chaperonin 60.1 and its peptides when compared to their wild type counterpart C57b1/6 mice. Spleen cells from TLR2KO mice were also refractory in their ability to produce IL-12 in response to the chaperonin and its peptides.

This in vitro study shows biological activity of these peptide fragments is mediated by the activation of TLR2 and TLR4 (FIG. 9).

Example 4

The Effect of Chaperonin Peptides In vivo

We next investigated the effect of low concentrations of Cpn60.1 and Cpn60.1-peptide 4 on allergic airways inflammation in light of the results obtained from the in vitro studies described earlier.

In order to perform these experiments we have slightly modified our protocol of immunization. Allergic inflammation in the lung is induced by 2 intra-nasal instillations of 10 μg of ovalbumin (OVA) in 100 μg of alum with 7 days interval between them. Control animals receive alum only. On day 14, all animals are exposed to an aerosol of OVA for 25 minutes, once a day for 3 consecutive days. All measurements are performed 24 h after the last antigen challenge.

We have shown that intra-nasal administration of Cpn60.1 (1 μg) significantly inhibited the total number of cells recruited to the lungs following acute antigen challenge (FIG. 10). The effect of Cpn60.1 and peptide 4 on the eosinophil recruitment to the airways was more profound (FIG. 11). Both low dose Cpn60.1 (0.1 and 1 μg) and peptide 4 (0.005 μg) caused a significant reduction in the recruitment of eosinophils which was not caused by an interference with the production of IL-5 from inflammatory cells (FIG. 12). Interestingly, low dose of peptide 4 affected total IgE production in this allergic model (FIG. 13).

Example 5

Cpn60.1 in Models of Pain

The effect of Cpn60.1 has been investigated in 2 models of pain, Complete Freund's Adjuvant (CFA)-induced hyperalgesia and Ultra Violet Burn-induced hyperalgesia. Mechanical hyperalgesia was measured using Von Frey filaments applied with increasing force to the hind paw. Thermal hyperalgesia was measured using the time taken to withdraw the hind paw from a heat source. Cpn60.1 (50 & 500 μg/kg) was chronically administered to male Wistar rats (200 g) subcutaneously for 7 days. Every alternate day behavioural responses to mechanical and thermal allodynia were recorded. After baseline recordings, CFA was injected in to the hind paw to induce hyperalgesia and behavioural tests were performed. Neither dose of Cpn60.1 reduced CFA-induced hyperalgesia compared to the control, ibuprofen (100 mg/kg) (FIGS. 14 and 15). Another model of hyperalgesia was tested, this time using UV burn to induce allodynia. Again, Cpn60.1 had little effect at inhibiting hyperalgesia compared to the group treated with ibuprofen (FIGS. 16 and 17).

Example 6

In vitro Studies on Human Inflammatory Cells

We have established a human monocyte assay to compare the efficacy of Cpn60.1 and various peptide sequences of this protein. Human monocytes were obtained by density-dependent centrifugation from peripheral venus blood from healthy volunteers. Monocytes were then isolated and purified with cells adjusted to a density of $2\times10^6$ cells/ml which were incubated for 1 hour 30 minutes. The plates were then washed twice with Hanks solution. 0.9 ml of RPMI medium was then added to each well followed by polymyxin-B (5 μg/ml). 30 minutes later, 0.1 ml of Cpn at 0.0001-1000 ng/ml or peptides were added to the wells. Cells were then incubated at 37° C., 5% $CO_2$ for 1 hour. The medium was removed and cells washed. 0.9 ml of medium was added to each well followed by 0.1 ml of LPS (1 ng/ml) and left to incubate for 24 hours. Supernatant was taken from each well and frozen for Enzyme Linked Immunosorbent Assay (ELISA).

We have demonstrated that Cpn60.1 alone, is able to stimulate human monocytes to induce TNF-alpha secretion but when added to an already established inflammatory stimulus (i.e. in the presence of LPS), Cpn60.1 inhibited TNF-alpha secretion at low doses (1 ng/ml) (FIG. 18). In contrast, Cpn10, failed to inhibit TNF-alpha secretion from human monocytes (FIG. 20). However, the protein appears to have a degree of LPS contamination and in the presence of polymyxin B, this contamination is reduced (FIG. 19). This potential confounding with LPS contamination is avoided when using the peptide sequences of Cpn60.1. The peptides also appeared to inhibit TNF-alpha secretion at low concentrations (FIG. 21).

Example 7

Cpn60.1 in Models of Non-allergic Inflammation

Because of the inhibitory effect in human inflammatory cells, we investigated whether Cpn60.1 is able to inhibit neutrophil recruitment in an in vivo system. To support this further, Riffo-Vasquez et al. have recently showed that *M. tuberculosis* chaperones can suppress eosinophil recruitment and bronchial hyper-responsiveness in a murine model of allergic inflammation (Riffo-Vasquez Y, Spina D, Page C et al. Effect of *Mycobacterium tuberculosis* chaperonins on bronchial eosinophilia and hyper-responsiveness in a murine model of allergic inflammation. *Clin. Exp Allergy,* 2004; 34(5); 712-719).

Female Balb/c mice were pre-treated intranasally with Cpn60.1 (1 µg/ml) for 3 days in the absence or following pre-treatment with polymyxin B (5 µg/ml) to rule out any effect of LPS contamination. 30 minutes after the last dose of Cpn60.1, mice were treated with LPS (1 µg/ml). Neutrophil influx and TNF-alpha release in the lungs were determined by bronchoalveolar lavage 24 hours later. LPS induced a dose dependent increase in neutrophilia compared to control (FIG. 22). Interestingly, the group pre-treated with Cpn60.1 showed suppression in neutrophilia but TNF-alpha secretion was not significantly attenuated (FIG. 24). The treatment of mice with polymyxin B made no difference to the ability of Cpn60.1 to suppress neutrophil recruitment indicating that this effect cannot be explained by contamination with LPS. No neutrophil recruitment was observed in mice treated with Cpn60.1 alone further enabling that any contamination with LPS failed to cause neutrophilia (FIG. 23).

Example 8

Exemplary Pharmaceutical Formulations

Whilst it is possible for a molecule of the invention to be administered alone, it is preferable to present it as a pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen-free.

The following examples illustrate medicaments and pharmaceutical compositions according to the invention in which the active ingredient is a molecule of the invention.

Preferably, the molecule of the invention is provided in an amount from 10 µg to 500 mg. It will be appreciated that the following exemplary medicaments and pharmaceutical compositions may be prepared containing an amount of the molecule of the invention from 10 µg to 500 mg. For example, the molecule of the invention may be present in a $10^{th}$ or $100^{th}$ or $200^{th}$ or $500^{th}$ of the amount shown in the following exemplary medicaments and pharmaceutical compositions with the amounts of the remaining ingredients changed accordingly.

Example A

Tablet

| Active ingredient | 1 mg |
|---|---|
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

Example B

Ophthalmic Solution

| Active ingredient | 1 mg |
|---|---|
| Sodium chloride, analytical grade | 0.9 g |
| Thiomersal | 0.001 g |
| Purified water to | 100 ml |
| pH adjusted to | 7.5 |

Example C

Tablet Formulations

The following formulations A and B are prepared by wet granulation of the ingredients with a solution of povidone, followed by addition of magnesium stearate and compression.

Formulation A

|  | mg/tablet | mg/tablet |
|---|---|---|
| (a) Active ingredient | 1 | 1 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
|  | 251 | 51 |

Formulation B

|  | mg/tablet | mg/tablet |
|---|---|---|
| (a) Active ingredient | 1 | 1 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
|  | 251 | 51 |

Formulation C

|  | mg/tablet |
| --- | --- |
| Active ingredient | 1 |
| Lactose | 200 |
| Starch | 50 |
| Povidone | 5 |
| Magnesium stearate | 4 |
|  | 260 |

The following formulations, D and E, are prepared by direct compression of the admixed ingredients. The lactose used in formulation E is of the direction compression type.

Formulation D

|  | mg/capsule |
| --- | --- |
| Active Ingredient | 1 |
| Pregelatinised Starch NF15 | 150 |
|  | 151 |

Formulation E

|  | mg/capsule |
| --- | --- |
| Active Ingredient | 1 |
| Lactose | 150 |
| Avicel ® | 100 |
|  | 251 |

Formulation F (Controlled Release Formulation)

The formulation is prepared by wet granulation of the ingredients (below) with a solution of povidone followed by the addition of magnesium stearate and compression.

|  | mg/tablet |
| --- | --- |
| (a) Active Ingredient | 1 |
| (b) Hydroxypropylmethylcellulose (Methocel K4M Premium) ® | 112 |
| (c) Lactose B.P. | 53 |
| (d) Povidone B.P.C. | 28 |
| (e) Magnesium Stearate | 7 |
|  | 201 |

Drug release takes place over a period of about 6-8 hours and was complete after 12 hours.

Example D

Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
| --- | --- |
| (a) Active ingredient | 1 |
| (b) Lactose B.P. | 143 |
| (c) Sodium Starch Glycolate | 25 |
| (d) Magnesium Stearate | 2 |
|  | 171 |

Formulation C

|  | mg/capsule |
| --- | --- |
| (a) Active ingredient | 1 |
| (b) Macrogol 4000 BP | 350 |
|  | 351 |

Capsules are prepared by melting the Macrogol 4000 BP, dispersing the active ingredient in the melt and filling the melt into a two-part hard gelatin capsule.

Formulation D

|  | mg/capsule |
| --- | --- |
| Active ingredient | 1 |
| Lecithin | 100 |
| *Arachis* Oil | 100 |
|  | 201 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
| --- | --- |
| (a) Active ingredient | 1 |
| (b) Microcrystalline Cellulose | 125 |
| (c) Lactose BP | 125 |
| (d) Ethyl Cellulose | 13 |
|  | 264 |

Example E

Injectable Formulation

| Active ingredient | 1 mg |
| --- | --- |
| Sterile, pyrogen free phosphate buffer (pH 7.0) to 10 ml | |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F

Intramuscular injection

| | |
|---|---|
| Active ingredient | 1 mg |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G

Syrup Suspension

| | |
|---|---|
| Active ingredient | 1 mg |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H

Suppository

| | mg/suppository |
|---|---|
| Active ingredient (63 μm)* | 1 |
| Hard Fat, BP (Witepsol H15 - Dynamit Nobel) | 1770 |
| | 1771 |

*The active ingredient is used as a powder wherein at least 90% of the particles are of 63 μm diameter or less.

One fifth of the Witepsol H15 is melted in a steam jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I

Pessaries

| | mg/pessary |
|---|---|
| Active ingredient | 1 |
| Anhydrate Dextrose | 380 |
| Potato Starch | 363 |
| Magnesium Stearate | 7 |
| | 751 |

The above ingredients are mixed directly and pessaries prepared by direct compression of the resulting mixture.

Example 9

Treatment of a Non-cancerous Disorder Using a Molecule of the Invention

A patient with arthritis is administered 1 mg of an agent of the invention per day intramuscularly or a depot preparation delivering this dose according to the methods of the invention.

Example 10

Methods of Pain Relief

The molecules of the invention will provide effective pain relief in the following incidences of pain: backache, headache, toothache, earache, Arthritis, Gout, soft tissue trauma, ligament/tendon traumatic damage, broken bones, Cancer, post operative pain, menstrual pain, obstetric pain, renal tract pain, visceral pain, burns, abscesses and other infections.

The suggested treatment route and regimen for the treatment of any of these conditions is the administration of 0.1 mg to 1 gram once every 12 hours by inhalation delivered via an inhaler. However the skilled person would know that the most appropriate treatment regime would be dependent on the individual and the severity of the pain being felt.

What is claimed is:

1. A chemically synthesized peptide molecule consisting of the polypeptide sequence:
DGSVVVNKVSELPAGHGLNVNTLSYGDLAAD (SEQ ID NO: 8).

2. A peptide molecule as defined in claim 1 for use in medicine.

3. A pharmaceutical composition comprising or consisting of a peptide molecule as defined in claim 1, and a pharmaceutically-acceptable excipient.

4. A method of treating allergic airways diseases in a patient comprising the step of administering to a patient in need thereof an effective amount of a peptide molecule as defined in claim 1.

* * * * *

SEQUENCE LISTING

<160> NUMBER OF SEQ ID NOS: 12

<210> SEQ ID NO 1
<211> LENGTH: 29
<212> TYPE: PRT
<213> ORGANISM: Mycobacterium tuberculosis

<400> SEQUENCE: 1

```
Met Ser Lys Leu Ile Glu Tyr Asp Glu Thr Ala Arg Arg Ala Met Glu
1               5                   10                  15

Val Gly Met Asp Lys Leu Ala Asp Thr Val Arg Val Thr
            20                  25
```

<210> SEQ ID NO 2
<211> LENGTH: 21
<212> TYPE: PRT
<213> ORGANISM: Mycobacterium tuberculosis

<400> SEQUENCE: 2

```
Leu Gly Pro Arg Gly Arg His Val Val Leu Ala Lys Ala Phe Gly Gly
1               5                   10                  15

Pro Thr Val Thr Asn
            20
```

<210> SEQ ID NO 3
<211> LENGTH: 33
<212> TYPE: PRT
<213> ORGANISM: Mycobacterium tuberculosis

<400> SEQUENCE: 3

```
Asp Gly Val Thr Val Ala Arg Glu Ile Glu Leu Glu Asp Pro Phe Glu
1               5                   10                  15

Asp Leu Gly Ala Gln Leu Val Lys Ser Val Ala Thr Lys Thr Asn Asp
            20                  25                  30

Val
```

<210> SEQ ID NO 4
<211> LENGTH: 28
<212> TYPE: PRT
<213> ORGANISM: Mycobacterium tuberculosis

<400> SEQUENCE: 4

```
Ala Gly Asp Gly Thr Thr Thr Ala Thr Ile Leu Ala Gln Ala Leu Ile
1               5                   10                  15

Lys Gly Gly Leu Arg Leu Val Ala Ala Gly Val Asn
            20                  25
```

<210> SEQ ID NO 5
<211> LENGTH: 25
<212> TYPE: PRT
<213> ORGANISM: Mycobacterium tuberculosis

<400> SEQUENCE: 5

```
Pro Ile Ala Leu Gly Val Gly Ile Gly Lys Ala Ala Asp Ala Val Ser
1               5                   10                  15

Glu Ala Leu Leu Ala Ser Ala Thr Pro
            20                  25
```

<210> SEQ ID NO 6
<211> LENGTH: 27
<212> TYPE: PRT
<213> ORGANISM: Mycobacterium tuberculosis

<400> SEQUENCE: 6

```
Glu Glu Gly Ile Val Pro Gly Gly Gly Ala Ser Leu Ile His Gln Ala
1               5                   10                  15

Arg Lys Ala Leu Thr Glu Leu Arg Ala Ser Leu
            20                  25
```

-continued

<210> SEQ ID NO 7
<211> LENGTH: 28
<212> TYPE: PRT
<213> ORGANISM: Mycobacterium tuberculosis

<400> SEQUENCE: 7

Thr Gly Asp Glu Val Leu Gly Val Asp Val Phe Ser Glu Ala Leu Ala
1               5                   10                  15

Ala Pro Leu Phe Trp Ile Ala Ala Asn Ala Gly Leu
            20                  25

<210> SEQ ID NO 8
<211> LENGTH: 31
<212> TYPE: PRT
<213> ORGANISM: Mycobacterium tuberculosis

<400> SEQUENCE: 8

Asp Gly Ser Val Val Asn Lys Val Ser Glu Leu Pro Ala Gly His
1               5                   10                  15

Gly Leu Asn Val Asn Thr Leu Ser Tyr Gly Asp Leu Ala Ala Asp
            20                  25                  30

<210> SEQ ID NO 9
<211> LENGTH: 31
<212> TYPE: PRT
<213> ORGANISM: Mycobacterium tuberculosis

<400> SEQUENCE: 9

Gly Val Ile Asp Pro Val Lys Val Thr Arg Ser Ala Val Leu Asn Ala
1               5                   10                  15

Ser Ser Val Ala Arg Met Val Leu Thr Thr Glu Thr Val Val Val
            20                  25                  30

<210> SEQ ID NO 10
<211> LENGTH: 25
<212> TYPE: PRT
<213> ORGANISM: Mycobacterium tuberculosis

<400> SEQUENCE: 10

Leu Thr Thr Glu Thr Val Val Val Asp Lys Pro Ala Lys Ala Glu Asp
1               5                   10                  15

His Asp His His His Gly His Ala His
            20                  25

<210> SEQ ID NO 11
<211> LENGTH: 539
<212> TYPE: PRT
<213> ORGANISM: Mycobacterium tuberculosis

<400> SEQUENCE: 11

Met Ser Lys Leu Ile Glu Tyr Asp Glu Thr Ala Arg Arg Ala Met Glu
1               5                   10                  15

Val Gly Met Asp Lys Leu Ala Asp Thr Val Arg Val Thr Leu Gly Pro
            20                  25                  30

Arg Gly Arg His Val Val Leu Ala Lys Ala Phe Gly Gly Pro Thr Val
        35                  40                  45

Thr Asn Asp Gly Val Thr Val Ala Arg Glu Ile Glu Leu Glu Asp Pro
    50                  55                  60

Phe Glu Asp Leu Gly Ala Gln Leu Val Lys Ser Val Ala Thr Lys Thr
65                  70                  75                  80

Asn Asp Val Ala Gly Asp Gly Thr Thr Thr Ala Thr Ile Leu Ala Gln

```
                         85                  90                  95
Ala Leu Ile Lys Gly Gly Leu Arg Leu Val Ala Gly Val Asn Pro
                100                 105                 110

Ile Ala Leu Gly Val Gly Ile Gly Lys Ala Ala Asp Ala Val Ser Glu
            115                 120                 125

Ala Leu Leu Ala Ser Ala Thr Pro Val Ser Gly Lys Thr Gly Ile Ala
            130                 135                 140

Gln Val Ala Thr Val Ser Ser Arg Asp Glu Gln Ile Gly Asp Leu Val
145                 150                 155                 160

Gly Glu Ala Met Ser Lys Val Gly His Asp Gly Val Val Ser Val Glu
                165                 170                 175

Glu Ser Ser Thr Leu Gly Thr Glu Leu Glu Phe Thr Glu Gly Ile Gly
                180                 185                 190

Phe Asp Lys Gly Phe Leu Ser Ala Tyr Phe Val Thr Asp Phe Asp Asn
            195                 200                 205

Gln Gln Ala Val Leu Glu Asp Ala Leu Ile Leu Leu His Gln Asp Lys
210                 215                 220

Ile Ser Ser Leu Pro Asp Leu Leu Pro Leu Leu Glu Lys Val Ala Gly
225                 230                 235                 240

Thr Gly Lys Pro Leu Leu Ile Val Ala Glu Asp Val Glu Gly Glu Ala
                245                 250                 255

Leu Ala Thr Leu Val Val Asn Ala Ile Arg Lys Thr Leu Lys Ala Val
                260                 265                 270

Ala Val Lys Gly Pro Tyr Phe Gly Asp Arg Arg Lys Ala Phe Leu Glu
            275                 280                 285

Asp Leu Ala Val Val Thr Gly Gly Gln Val Val Asn Pro Asp Ala Gly
            290                 295                 300

Met Val Leu Arg Glu Val Gly Leu Glu Val Leu Gly Ser Ala Arg Arg
305                 310                 315                 320

Val Val Val Ser Lys Asp Asp Thr Val Ile Val Asp Gly Gly Gly Thr
                325                 330                 335

Ala Glu Ala Val Ala Asn Arg Ala Lys His Leu Arg Ala Glu Ile Asp
                340                 345                 350

Lys Ser Asp Ser Asp Trp Asp Arg Glu Lys Leu Gly Glu Arg Leu Ala
            355                 360                 365

Lys Leu Ala Gly Gly Val Ala Val Ile Lys Val Gly Ala Ala Thr Glu
            370                 375                 380

Thr Ala Leu Lys Glu Arg Lys Glu Ser Val Glu Asp Ala Val Ala Ala
385                 390                 395                 400

Ala Lys Ala Ala Val Glu Glu Gly Ile Val Pro Gly Gly Gly Ala Ser
                405                 410                 415

Leu Ile His Gln Ala Arg Lys Ala Leu Thr Glu Leu Arg Ala Ser Leu
            420                 425                 430

Thr Gly Asp Glu Val Leu Gly Val Asp Val Phe Ser Glu Ala Leu Ala
            435                 440                 445

Ala Pro Leu Phe Trp Ile Ala Ala Asn Ala Gly Leu Asp Gly Ser Val
            450                 455                 460

Val Val Asn Lys Val Ser Glu Leu Pro Ala Gly His Gly Leu Asn Val
465                 470                 475                 480

Asn Thr Leu Ser Tyr Gly Asp Leu Ala Ala Asp Gly Val Ile Asp Pro
                485                 490                 495

Val Lys Val Thr Arg Ser Ala Val Leu Asn Ala Ser Ser Val Ala Arg
            500                 505                 510
```

```
Met Val Leu Thr Thr Glu Thr Val Val Asp Lys Pro Ala Lys Ala
            515                 520                 525

Glu Asp His Asp His His Gly His Ala His
            530                 535

<210> SEQ ID NO 12
<211> LENGTH: 540
<212> TYPE: PRT
<213> ORGANISM: Mycobacterium tuberculosis

<400> SEQUENCE: 12

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
```

```
                340                 345                 350
Asn Ser Asp Ser Asp Tyr Asp Arg Glu Lys Leu Gln Glu Arg Leu Ala
        355                 360                 365
Lys Leu Ala Gly Gly Val Ala Val Ile Lys Ala Gly Ala Ala Thr Glu
        370                 375                 380
Val Glu Leu Lys Glu Arg Lys His Arg Ile Glu Asp Ala Val Arg Asn
385                 390                 395                 400
Ala Lys Ala Ala Val Glu Glu Gly Ile Val Ala Gly Gly Val Thr
                405                 410                 415
Leu Leu Gln Ala Ala Pro Thr Leu Asp Glu Leu Lys Leu Glu Gly Asp
                420                 425                 430
Glu Ala Thr Gly Ala Asn Ile Val Lys Val Ala Leu Glu Ala Pro Leu
            435                 440                 445
Lys Gln Ile Ala Phe Asn Ser Gly Leu Glu Pro Gly Val Val Ala Glu
        450                 455                 460
Lys Val Arg Asn Leu Pro Ala Gly His Gly Leu Asn Ala Gln Thr Gly
465                 470                 475                 480
Val Tyr Glu Asp Leu Leu Ala Ala Gly Val Ala Asp Pro Val Lys Val
                485                 490                 495
Thr Arg Ser Ala Leu Gln Asn Ala Ala Ser Ile Ala Gly Leu Phe Leu
            500                 505                 510
Thr Thr Glu Ala Val Val Ala Asp Lys Pro Glu Lys Glu Lys Ala Ser
            515                 520                 525
Val Pro Gly Gly Gly Asp Met Gly Gly Met Asp Phe
530                 535                 540
```